US008398603B2

(12) United States Patent
Thirstrup et al.

(10) Patent No.: US 8,398,603 B2
(45) Date of Patent: Mar. 19, 2013

(54) LEAK SENSOR

(75) Inventors: Carsten Thirstrup, Charlottenlund (DK); Daniel Nilsson, Malmo (SE); Henrik Pranov, Copenhagen (DK); Lars Lading, Roskilde (DK)

(73) Assignee: Coloplast A/S, Humlebaek (DK)

( * ) Notice: Subject to any disclaimer, the term of this patent is extended or adjusted under 35 U.S.C. 154(b) by 775 days.

(21) Appl. No.: 12/224,507

(22) PCT Filed: Feb. 20, 2007

(86) PCT No.: PCT/DK2007/000096
§ 371 (c)(1),
(2), (4) Date: Sep. 28, 2009

(87) PCT Pub. No.: WO2007/098762
PCT Pub. Date: Sep. 7, 2007

(65) Prior Publication Data
US 2010/0030167 A1 Feb. 4, 2010

(30) Foreign Application Priority Data

Feb. 28, 2006 (DK) ................................ 2006 00289
Apr. 25, 2006 (DK) ................................ 2006 00603

(51) Int. Cl.
*A61M 1/00* (2006.01)
(52) U.S. Cl. .......................................... 604/304; 602/41
(58) Field of Classification Search .................. 604/304, 604/336, 338, 339, 343, 344, 361; 602/52, 602/54, 56; 60/300
See application file for complete search history.

(56) References Cited

U.S. PATENT DOCUMENTS 3,832,510 A * 8/1974 Pfau et al. .................. 219/69.13
4,754,264 A 6/1988 Okada et al.
(Continued)

FOREIGN PATENT DOCUMENTS

DE 199 53 062 A1 5/2000
EP 1188157 B1 12/2005
(Continued)

OTHER PUBLICATIONS

Datasheet for Maxim MAX951 circuit, http://www.datasheets.org.uk/MAX951-datasheet.html, 2001.*
(Continued)

*Primary Examiner* — Melanie Hand
(74) *Attorney, Agent, or Firm* — Coloplast Corp., Coloplast A/S; Daniel G. Chapik; Nicholas R. Baumann

(57) ABSTRACT

The present invention relates to a method and dressing for detecting detachment of the dressing, which is applied to a surface of an at least partly electrically conductive object. The dressing comprises an adhesive for attaching the dressing to the electrically conductive object and at least two electrodes arranged in a distance from the electrically conductive object. A voltage is applied to the first and second electrode establishing an electrical circuit comprising a first capacitor between the first electrode and the electrically conductive object and a second capacitor between the second electrode and the electrically conductive object. Changes of the capacitance between at least one of the first and the second electrode and the electrically conductive object are detected, and an alarm is activated when the changes of the capacitance reach a predetermined value. This advantageously provides a method whereby a leak can be detected quickly. Furthermore, this advantageously provides a leak sensor with no direct physical or mechanical contact between the electrically conductive object, e.g. the skin, and the electrodes. This provides for a dressing comprising a leak sensor without compromising the comfort of the user.

22 Claims, 16 Drawing Sheets

U.S. PATENT DOCUMENTS

| | | | |
|---|---|---|---|
| 5,593,397 A | 1/1997 | La Gro | |
| 5,879,292 A | 3/1999 | Sternberg et al. | |
| 6,025,725 A | 2/2000 | Gershenfeld et al. | |
| 6,171,289 B1 * | 1/2001 | Millot et al. | 604/336 |
| 2003/0169032 A1 | 9/2003 | Minchole et al. | |

FOREIGN PATENT DOCUMENTS

| | | |
|---|---|---|
| GB | 2 343 628 A | 5/2000 |
| WO | WO 94/15562 | 7/1994 |
| WO | WO 00/79497 A1 | 12/2000 |
| WO | WO 02/099765 A1 | 12/2002 |

OTHER PUBLICATIONS

Akar, O., et al., Sensors and Actuators, vol. A95, pp. 29-38, 2001.

Zeng, K., et al., Rev. Sci. Inst., vol. 73, p. 4375, 2002.

Ong, K.G., et al., Sens. Act., vol, A93, p. 33, 2001.

Ashrafi, R., et al., Rev. Sci. Inst., vol, 70, p. 3483, 1999.

Ignjatovic, Z., et al., IEEE Sensors Journal, vol, 6, p. 403, 2005.

Akar, O., et al., "A Wireless Batch Sealed Absolute Capacitive Pressure Sensor," Sensors and Actuators, vol. A95, pp. 29-38, 2001.

Zeng, K., et al., "Time Domain Characterization of Oscillating Sensors: Application of Frequency Counting to Resonance Frequency Determination," Review of Scientific Instruments, vol. 73, p. 4375, 2002.

Ong, K.G., et al., "Design and Application of a Wireless, Passive, Resonant-Circuit Environmental Monitoring Sensor," Sensors and Actuators, vol, A93, p. 33, 2001.

Ashrafi, R., et al., "A High Precision Method for Measuring Very Small Capacitance Changes," Review of Scientific Instruments, vol, 70, p. 3483, 1999.

Ignjatovic, Z., "An Interface Circuit for Measuring Capacitance Changes Based Upon Capacitance-to-Duty Cycle (CDC) Converter", IEEE Sensors Journal, vol. 5, No. 3, pp. 403-405, 2005.

* cited by examiner (a)

(b)

(a)

(b)

(c)

(d)

(a)

(b)

LEAK SENSOR

This is a national stage of PCT/DK2007/000096 filed Feb. 20, 2007 and published in English.

BACKGROUND OF THE INVENTION

1. Field of the Invention

The present invention relates to a method, a dressing and a dressing assembly for detecting a leak between the dressing and an electrically conductive object by measuring the changes in capacitance between the dressing and the electrically conductive object.

2. Description of the Related Art

Some stoma patients experience problems with leakage from ostomy bags or leakage of body fluids from the ostomy. Origins of the leakages can be skin folds developed underneath the adhesive of a bandage, a scar near a stoma not providing good adhesion or presence of a humid spot prior to attaching the adhesive and thereby preventing the adhesive from obtaining good adhesion to the skin or the leak may occur in time as the adhesive properties of the bandage deteriorate. A leakage for a stoma patient can be embarrassing and highly inconvenient. Also wound care patients can have problems with leakages from a dressing. A patient may withdraw from social contact because of the smell or the sight of exudates leaking from a wound.

With an increasing elderly population in many countries, national health care systems have much focus on the total cost. For stoma patients or chronic wound patients, the bandages or the dressings are often changed regularly by a caring nurse. Extending the length of time a bandage or a dressing can remain on the stoma or wound reduces the need for care, enabling a reduction in health care costs.

An early warning reporting system either to the patient or to the caring nurse that a bandage or a dressing needs to be changed would therefore be useful. Not only will the patient avoid unpleasant accidents, helping the patient to feel confident and secure in his or her daily, life, but it may also reduce the cost of our health care systems.

There is therefore a need of a sensor, which is able to report to the patient himself or herself or to a caring nurse, when leakage starts to occur in a bandage or a dressing and it needs to be changed. However, it is important that the sensor triggering such an alarm has a high degree of reliability, i.e. essentially no false negative alarms, and that it can provide a fast response enabling the patient or the nurse sufficient time to change the bandage or the dressing.

U.S. Pat. No. 4,754,264 discloses a water detecting device for a diaper based on sensing the degree of wetness by positioning two capacitor electrodes in the diaper detecting a liquid being absorbed by a water permeable sheet covering the two electrodes. The water permeable sheet causes a change in the dielectric constant of the electrostatic capacitance between the two electrodes and a detecting circuit detecting a change of the electrostatic capacitance transmitting a signal indicating that the diaper is wet. The U.S. Pat. No. 4,754,264 makes use of the fact that a medium comprising a water absorbing material gets wet, but the water has flown from the source to the permeable sheet, before it gets absorbed. It is therefore not suitable to detect a leak before it has wetted the medium.

WO02/099765 discloses a resonance circuit arranged on an insulating substrate with at least one pair of spaced measuring electrodes arranged in parallel or in series with the resonance circuit in such a manner that a material able to change its electrical conductivity under external influence can be placed or can pass through in the space between the measuring electrodes. Measuring the change of the resonance frequency or the Q-factor of the resonance circuit permits measuring and surveying the electrical conductivity of a material and measure changes under external influence such as e.g. moisture and temperature. However, the invention makes use of a change in the electrical conductivity and the material to be measured needs to be placed between the two measuring electrodes. This method is therefore not suitable for detecting a leak at the interface between the skin and an adhesive, because this interface cannot in a practical way be placed between two measuring electrodes.

EP 1 188 157 discloses a radio frequency resonant circuit sensing device for detecting a fluid in an article or container, in particular a body fluid from a human or an animal. The device comprises a layered structure with two electrically conducting electrodes attached to a substrate and with a dielectric medium in between the two electrodes. The resonant circuit sensing device is contained within the article to be measured. The invention can be suitable for measuring if a wound bleeds or a stoma bag is filled. However, the body fluid to be measured needs to be guided to the space between the two electrically conducting electrodes. It is therefore not suitable for detecting a leak due to exudates of a wound or discharge from a stoma propagating between the skin and an adhesive to the periphery of a bandage or dressing.

GB 2 343 628 discloses a device measuring the conductivity of the adhesive of a seal for an ostomy bag. The measuring device comprises two series of microelectrodes arranged on two tracks of at least an arc of a circle whose centre is coincident with the centre of a through-passage to an ostomy. The microelectrodes have substantially the form of a small cylinder of metal and penetrate to about half the thickness of the adhesive composition. It is thus the conductivity of the adhesive between the two series of electrodes, which is measured.

However, such a device measuring the conductivity of the adhesive only makes a respond in the case, where the adhesive has lost its effectiveness and it is desirable to change the adhesive. Furthermore, as the device measures directly between the two series of electrodes, the device will not detect a leak occurring as a consequence of a skin-fold, a scar or a wet spot creating a channel for a leak and where a leak propagates between the skin and the adhesive.

There is therefore a need in the art of sensors of being able to detect leaks around the whole periphery of a stoma or a wound propagating between the skin of a person and the adhesive of a bandage or a dressing in sufficient time before such a leak has propagated to the edge of the bandage or dressing.

An objective of the present invention is to provide a sensor detecting a leak between an adhesive of a bandage or dressing and the skin of a person or any other mammal making use of the skin as a ground plane for an alternating electrical current at frequencies, where the skin has a moderate or high conductivity.

Another objective of the present invention is to detect the leak in ample time before it has propagated completely to the edge of the bandage or dressing.

A further objective of the present invention is to provide sensitivity at the whole periphery of a stoma or a wound.

An even further objective of the present invention is to provide a sensor, which may be produced at high production throughput and at low cost.

An even further objective of the present invention is to provide a sensor which is disposable and which may be connected to a reader unit in a simple way.

An even further objective of the present invention is to provide a sensor reporting the condition of the adhesive of a bandage or a dressing of a wound to a patient, a caring nurse or a service centre.

SUMMARY OF THE INVENTION

Thus the present invention discloses a method for detecting detachment of a dressing, for example a bandage, patch or ostomy base plate, which is applied to a surface of an at least partly electrically conductive object, said dressing comprising an adhesive for attaching the dressing to the electrically conductive object and at least two electrodes arranged at a distance from the electrically conductive object, and wherein, a voltage Is applied to the first and second electrode establishing an electrical circuit comprising a first capacitor between the first electrode and the electrically conductive object and a second capacitor between the second electrode and the electrically conductive object; changes of the capacitance between at least one of the first and the second electrode and the electrically conductive object is detected; and an alarm is activated when the changes of the capacitance reach a predetermined value.

This advantageously provides a method whereby a leak can be detected quickly.

Furthermore, this advantageously provides dressing having a leak sensor with no direct physical or mechanical contact between the electrically conductive object, e.g. the skin, and the electrodes. This provides for a dressing comprising a leak sensor without compromising the comfort of the user.

When read in this text, the term 'conductive' should be read as 'electrically conductive' unless explicitly stated otherwise.

It should be understood that 'an at least partly electrically conductive object' may be an object comprising areas which are not conductive, while other areas are conductive, e.g. the skin of a person having a surface not being conductive except below that surface. Furthermore 'an at least partly electrically conductive object' may also be an object, which is only conductive when certain electrical signals are applied. Again, the skin of a person is an example where applying a direct current (DC), the skin practically exhibits no electrical conductivity. However, applying an alternating current (AC), the skin exhibits electrical conductivity, which is increasing several decades with increasing frequencies in the range from DC to approximately 100 MHz.

The electrodes can be formed of many different types of materials, for example metals like silver, gold, aluminium or copper or paste of silver or aluminium; conducting polymers like polyaniline, polypyrrole, ethylenedioxythiophene, poly (p-pyridyl vinylene); or amorphous conducting carbon films, films of conducting carbon fibres or polymer-conducting-carbon-black. Materials may also be alloys and/or semiconductors such as tin oxide ($SnO_2$), zinc oxide ($ZnO_2$), indium tin oxide (ITO) or the like.

Furthermore, the term 'alarm' should be understood broadly as being any type of means for drawing attention to the dressing. Such an alarm may be present on the dressing itself, such as a small vibrator, sound or light emitting element or a color indication. Alarms remote from the dressing may also be provided, for example personal computers, cellular phones or PDAs (Personal Digital Assistants) or iPods, which all are capable of using known means in order to obtain the attention of a person.

The predetermined value of the change of capacitance on which the alarm is activated may be of different types. For example, an alarm corresponding to a leak may be an increase in the magnitude of the capacitance, or a decrease in the magnitude of the capacitance, or it may be a time variation of the change of capacitance. Such a time variation of the change of capacitance may be an initial negative change of capacitance within a first predetermined period of time following by a positive change of capacitance within a second predetermined period of time. An alarm corresponding to a soaked adhesive may be a positive change of capacitance within a third predetermined period of time.

Typically, said first and said second predetermined period of time are shorter than said third predetermined period of time. Said first and said second predetermined period of time may be within 10 seconds to 30 minutes and said third predetermined period of time may be within 10 minutes to 100 hours or longer. Activation of alarms may be triggered by other types of predetermined values of the change of capacitance. The term predetermined value is thus not limited to a single value, but may also include a two-dimensional array of time and values of changes of capacitance. It may also include arrays of other variables such as changes of temperature, pressure and the like. The other variables may be measured by integrating other sensors such as temperature sensors and pressure sensors in the dressing and/or in the reader measuring changes of capacitance.

The terms 'dressing' and 'bandage' have been used alternating within the present text. Within the scope of the present invention these terms should be read identically. In general they both refer to an assembly of an adhesive, which is disposed on a backing layer. Said assembly can further comprise numerous additional components. For example the adhesive will typically be skin friendly as the assembly is to be applied to the human body. In some cases absorbent materials are added either in the adhesive or inserted between adhesive sections of the assembly, e.g. for wound dressings in order to absorb fluid from a wound. Hydrocolloid particles can also additionally/alternatively be added in the adhesive compound in order to further improve the adhesive and skin friendly properties of the adhesive. Such hydrocolloid adhesives are frequently used in a body side wafers within ostomy appliances, whether it is so-called one-piece or two-piece appliances. A body side wafer is applied to the skin around a stoma and holds the collecting bag for collecting stools from the stoma.

Furthermore, it should be understood, as would be appreciated by the person skilled in the art, that the terms resistance, capacitance and inductance all indicates a part or component having a numerical value, thus, throughout the application these may be realised by providing a resistor, capacitor and inductor, respectively.

In one embodiment, the changes of the capacitance may be detected by monitoring the frequency response of the electrical circuit. All resonance circuits, i.e. electrical circuits comprising a capacitance and an inductance, have a frequency response and such resonance circuits can be obtained by using few very simple components. Thus, a simple circuit comprising a few and low cost components may be provided in order to detect a leak, by transducing the leak into a time response or frequency response, which readily can be monitored.

The frequency response may be monitored using different methods. In one embodiment the frequency response of the electrical circuit is carried out by performing a frequency sweep at regular intervals while measuring the response from the electrical circuit. In another embodiment, the monitoring of the frequency response of the electrical circuit can be made applying an electrical impulse to the electrical circuit and subsequently measuring the response from the electrical circuit.

In another aspect of the invention, a dressing suitable for applying the method and its embodiments described herein is furthermore disclosed. Such a dressing according to the invention comprises an adhesive body having a proximal adhesive surface; at least a first and a second electrode arranged on the dressing so that at least a part of the adhesive body is arranged between the proximal adhesive surface and the first and second electrodes, wherein a first width of the first electrode and a second width of the second electrode are larger than the respective first thickness and second thickness of the respective first and second electrode in at least one area.

This allows for flat, very thin and compact dressings whereon the electrodes may be provided. This is possible since the capacitance is influenced by the width of the capacitor, i.e. the area of the surface parallel to the surface of the conductive object, and not the thickness of the electrodes. Thus, very thin electrodes may be provided. This advantageously allows for discreet and comfortable dressings, suitable for daily wear beneath the wearer's clothes.

It should be understood that the adhesive body exhibits primarily dielectric properties, i.e. shows a very low electric conductivity, in order to establish a capacitance between an electrode and the electrically conductive object, e.g. the skin of a person. Typically, before use the adhesive body has a "dielectric" value between 2 and 3.

For the adhesives of the embodiments of the present invention, the resistance of the adhesive between electrodes to the adhesive surface of the dressing, which is attached to the at least partly electrically conductive object like the skin of a mammal, is approximately given by $$R_{adh} = \rho_{adh} \frac{l_{adh}}{A},$$

where $\rho_{adh}$ is the resistivity the adhesive, $l_{adh}$ is the thickness of the adhesive, and A is the area of the first electrode. A non-conductive adhesive means that the adhesive exhibits dielectric properties and that $R_{adh}$ is larger than the other contributions to the resistance measured from any position on the first electrode to any position on a second electrode on top of the adhesive. Other contributions to the resistance are the resistance of the skin ([$R_{skin1}+R_{skin2}$ in FIG. 2(b)]) and the resistance of the electrodes. Typically, this means that the resistivity of the adhesive is larger than 0.1 Ωm, more preferably larger than $10^2$ Ωm, and even more preferable larger than $10^5$ Ωm. For embodiments, where a foil is disposed in between the adhesive and the first and second electrodes, the foil should be considered as a part of the adhesive with the same requirements for being non-conductive.

In one embodiment, the first and second width is uniform along the extent of the first and second electrode, respectively. This provides for uniform measurements independent of the position of the occurring leak.

In order to be able to detect a leak occurring around an area of interest, the second electrode at least partly encircles the first electrode. Additionally or alternatively at least one of the electrodes should enclose the area of interest in order to detect a leak before it enters, or alternatively exits, said area of interest.

The electrodes may be formed in many different forms and shapes. For example, they may be formed as tracks having many different paths, for example any known geometrical shape such as oval, square, triangular or alternatively have an irregular shape. In one preferred embodiment the first and the second electrode are formed as respective first and second circular track and where the inner diameter of the second circular track is larger than the outer diameter of the first circular track. This allows the electrodes to be simple to produce and that a signal representing a leak be the same independently of where the leak occurs along the electrodes.

In another embodiment of the dressing, an inductance may connect the first and second electrode. This provides an inductance whereby a resonance circuit is established and it may be possible to induce a current from a distance through the inductance, typically in the shape of a coil, thereby enabling wireless electromagnetic coupling to a reader circuit.

In an alternate embodiment, the first and the second electrode are electrically isolated from the adhesive body. Thus, direct contact between the electrodes and body liquids absorbed by the adhesive can be avoided.

In order to achieve a capacitance between the conductive object and the respective electrodes, the electrodes have to be arranged in a distance from the conductive object. Thus, in one embodiment the at least first and second electrode are arranged at least partly embedded in the adhesive body and in another embodiment the at least first and second electrode are arranged on the distal side of the adhesive body.

When the electrodes are at least partly embedded in the adhesive, a construction may be provided wherein the conductivity of the adhesive furthermore can be measured and such constructions are additionally or alternatively also solid and may be discretely hidden in the adhesive.

When the electrodes are arranged on the distal side of the adhesive, i.e. the opposite side of the proximal adhesive surface which is attached to the conductive object, the electrodes may be made easy accessible for different purposes such as measurement, replacement, monitoring etc.

In one embodiment, the first electrode and the second electrode are printed on a flexible film. This is one simple way of providing a dressing according to the invention as the film subsequently can be attached to the distal side of the adhesive body.

In another embodiment, an encircling groove is formed in the proximal adhesive surface of the adhesive body, encircling the centre of the bandage or dressing. The encircling groove may be arranged opposite one of the electrodes. This enhances the sensitivity of detecting a leak, as the response from the electrical circuit changes significantly when the content of groove changes, such as being filled with a liquid.

Furthermore a first electrically conductive ring and a second electrically conductive ring may be arranged in the encircling groove, and when the first electrically conductive ring is electrically connected to the first electrode and the second electrically conductive ring is electrically connected to the second electrode. A liquid filling the groove will practically create a short circuit or a strong capacitive coupling between the first conductive ring and the second conductive ring, which significantly will change the response from the circuit and thereby identifying a leak.

It should be understood that the invention disclosed herein is not limited to only two electrodes. Thus in another embodiment a third or more electrodes may encircle the first and the second electrode. A multitude of electrodes on the distal side of an adhesive may be advantageous for the detection of a leak. Each time the leak is below a particular electrode, a capacitance change related to that electrode may be detected. The scheme therefore enables detection of the course of a propagating leak.

In one embodiment according to the present invention, the dressing is a base plate of an ostomy bag. Thus means are provided to detect fluid leaking between the base plate and the skin, and it may be detected practically as soon as a leak occurs or even prior to the occurrence.

In order to eliminate ambient noise, a first upper electrode and a second upper electrode electrically connected by a second inductance can advantageously be arranged on the distal side of the first and second electrode. The first upper and the second upper electrode may record ambient disturbances such as capacitive coupling via a fluid in the ostomy bag and the signal from such disturbances may be subtracted from the signal coming from the first and second electrode thereby creating a resulting signal discriminating a leak from other events.

An additional way of eliminating ambient disturbances is introducing an electrically conductive shield layer on the distal side of the first and the second electrode with a dielectric medium between the shield layer and the electrodes.

In yet a different embodiment, the change in capacitance may be detected by monitoring the change in the time constant of the established electrical circuit. The time constant may for example be detected by a counter and an astable multivibrator, which is connected to the first and second capacitor via at least one resistor, thereby forming a resistor-capacitor circuit. It is well known that a time constant may be determined from such a circuit.

Other means for detecting the time constant may be provided. For example, instead of an astable multivibrator, the time constant of the electrical circuit may be detected by a Colpitts oscillator comprising the first and second capacitor and at least one inductor, and repetitively counting the change in the number of output pulses from the Colpitts oscillator within a predetermined time interval.

Thus, it may be understood by the person skilled in the art that many different types of oscillators may be used to arrive at the claimed invention.

In another aspect of the invention a shield for reducing capacitive coupling from ambient surroundings into the electrodes of the dressing is provided as described above. Such a shield is advantageously formed as an electrically conductive pattern, which is provided on the distal side of the at least first and second electrodes. Thus, more reliable detection of coming or occurring leaks can be provided.

It should be understood that by the distal side of the first and second electrodes it is referred to the side facing away from the surface whereon the dressing is attached.

Advantageously, when the dressing is a base plate connectable to an ostomy collection bag, the electrically conductive pattern can be arranged between the at least first and second electrodes and the ostomy collection bag to shield from capacitive coupling between the electrodes and the contents in the collection bag.

BRIEF DESCRIPTION OF THE DRAWINGS

The invention is disclosed more in details with reference the embodiments in the drawing in which.

DETAILED DESCRIPTION OF THE PRESENT INVENTION

Figure 1:
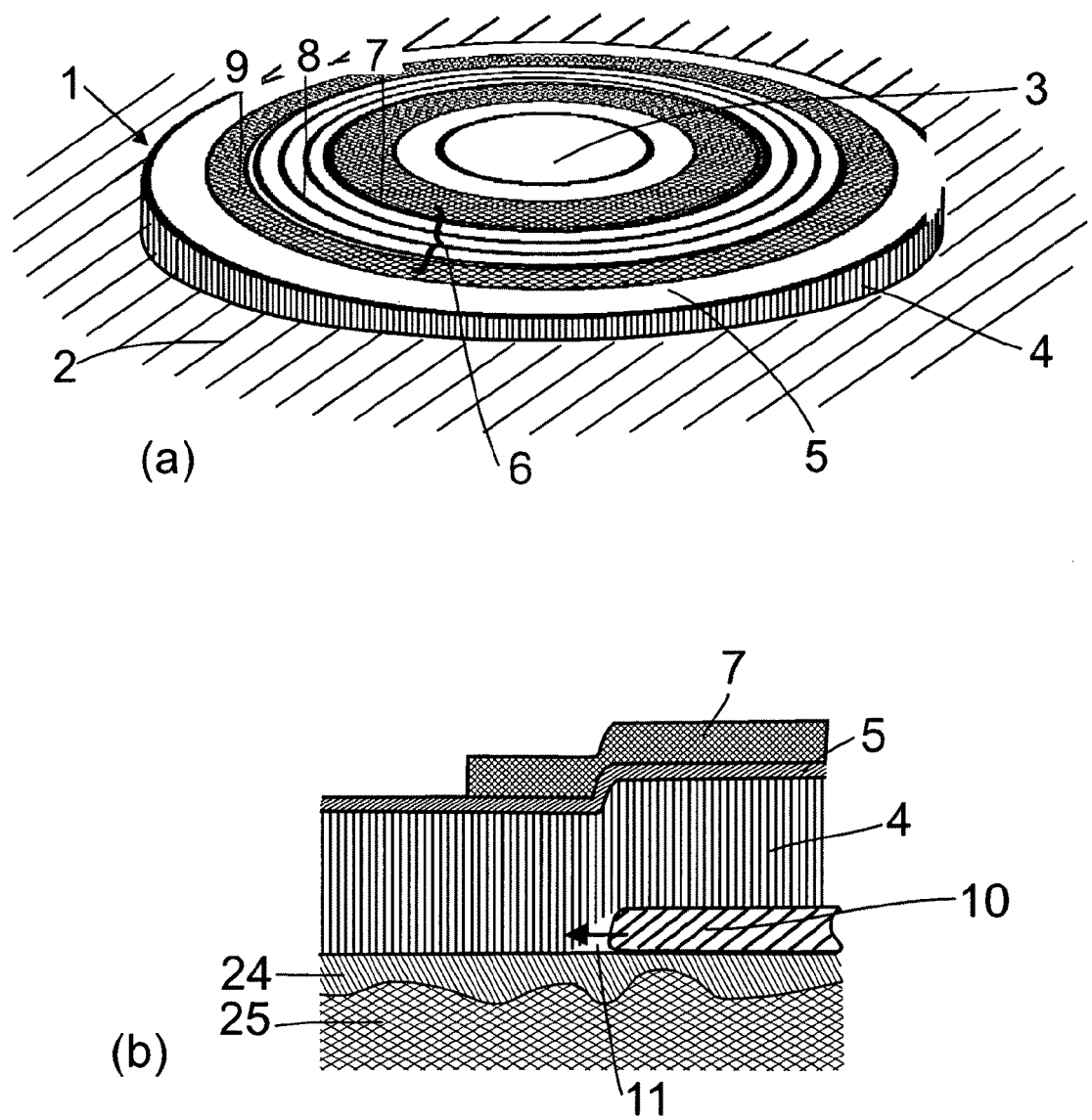
FIG. 1a shows a perspective view of an embodiment of a dressing according to the present invention.
FIG. 1b shows partly a cross-sectional view of the embodiment from FIG. 1a and a leak.

FIG. 1a shows schematically a bandage 1 attached to the skin of a mammal 2 comprising an opening 3, an adhesive 4, a top-foil 5 and a pattern of electrically conductive films 6. FIG. 1b is a partial cross-sectional view of the bandage with a leak 10 propagating from a stoma or a wound along the interface between the adhesive 4 and the surface of the skin. A gap 11 may also be created prior to the propagating leak. The skin is illustrated by an outer layer epidermis 24 of low conductivity and a middle layer of dermis with higher conductivity 25. The inner layer of hypodermis below the layer of dermis is not illustrated in FIG. 1b.

The bandage 1 may be used as an adhesive base plate for an ostomy bag (not shown). The base plate thus has an opening 3 to allow discharge from a stoma (not shown) to fill the ostomy bag attached to the base plate. In another embodiment, the bandage may be used as a dressing for a wound (not shown), wherein the opening 3 surrounds the wound and the dressing containing antibacterial and wound-healing compounds are placed in the opening 3 with the purpose of covering the wound.

It should however be understood that the present invention is not limited to base plates in ostomy and dressings in wound care, but covers other forms of detection of leakage of body fluids. An example is a fecal collector, which includes a bag having an opening for receiving fecal discharge and an attachment patch to be attached to the skin of a patient. Such a fecal collector is described e.g. in U.S. Pat. No. 5,593,397. The present invention could readily be integrated in the attachment patch of the fecal collector to provide a warning report of a fecal leakage.

When an alternating current is applied to the electrically conductive pattern, capacitive coupling occurs between the electrically conductive pattern on the top-foil and the skin. The conductive pattern 6 has an inner ring-capacitor 7, a coil 8 and an outer ring-capacitor 9. The top-foil 5 separates the electrically conductive film 6 from the adhesive 4. If the adhesive absorbs liquid, the top-foil prevents the liquid from being In physical contact with and short-circuiting the electrically conductive films.

Figure 2:
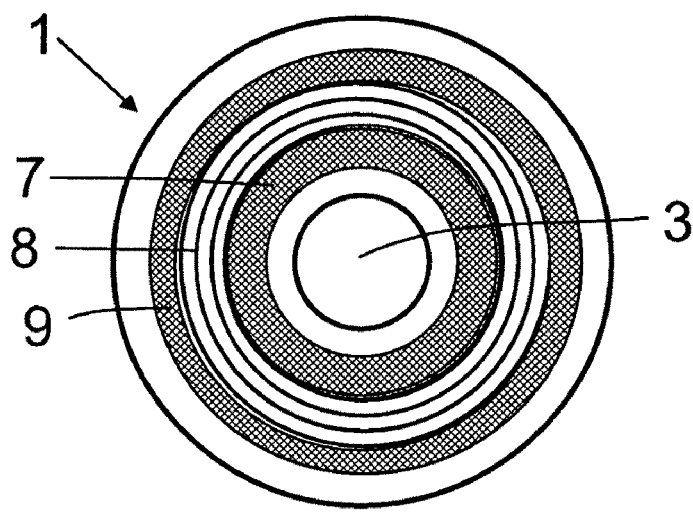
FIGS. 2a, 2b and 2c show the embodiment of FIGS. 1a and 1b, the electrical equivalent diagram thereof and schematically a plot of the frequency response change as a result of the change of capacitance.
Figure 2:
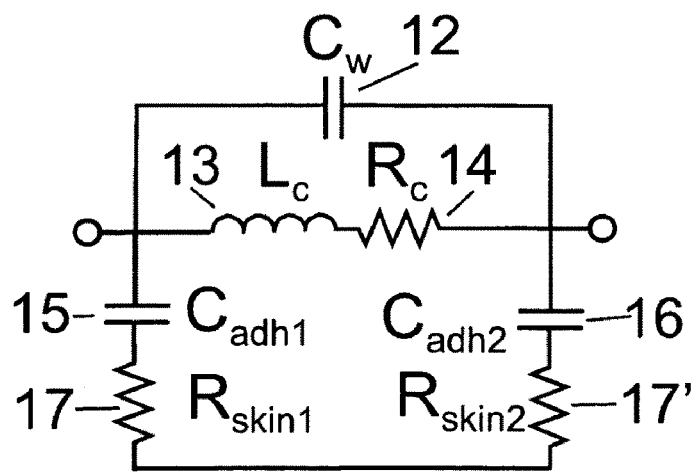
Figure 2:
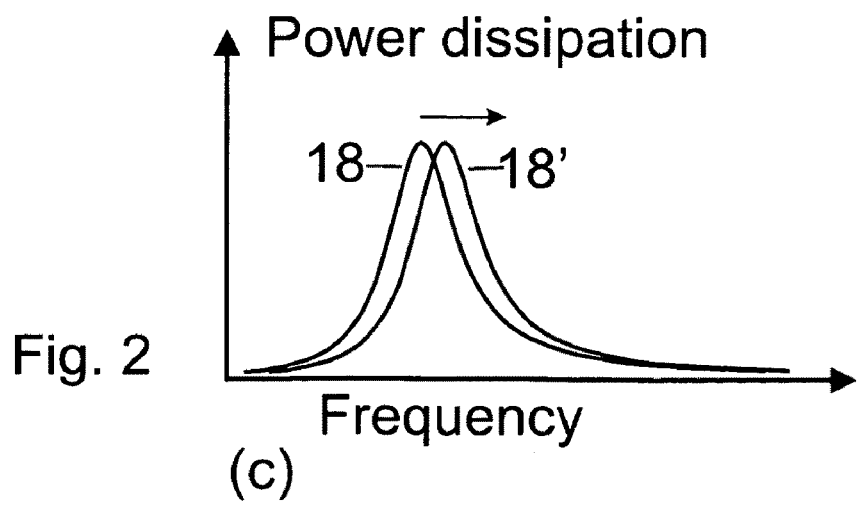

FIG. 2a shows a top-view of the bandage from FIG. 1a. FIG. 2b shows a first order electrical equivalent diagram with discrete components depicted. It is the equivalent diagram of the electrical circuit when the bandage is applied to the skin of a mammal, for example as in FIG. 1a. FIG. 2c shows schematically a plot of the power dissipated in the circuit diagram in FIG. 2b as a function of the applied frequency from an electromagnetic field coupling to the coil of the electrical circuit. In FIG. 2c, curves are plotted in the case of no leak 18 and in the case of a leak 18'. The discrete components represent the capacitance $C_w$ 12 between the wires of the coil 8 and between the two ring capacitors 7 and 9, an inductance $L_c$ 13, a series resistance $R_c$ 14, capacitance $C_{adh1}$ 15 between the inner ring of the electrically conductive film and the skin, capacitance $C_{adh2}$ 16 between the outer ring electrically conductive film and the skin, and the resistance of the skin $R_{skin1}$ 17 and $R_{skin2}$ 17'. Neglecting the resistance of the electrically conductive films $R_c$, and the capacitance between the wires and the two capacitive rings $C_w$, the resonance frequency is approximately given by $$f_{res} = \frac{1}{2\pi\sqrt{L_c C_{tot}}}, \quad \text{Eqn. 1}$$

where $C_{tot}$ is the series connection of the two capacitors $C_{adh1}$ and $C_{adh2}$ $$C_{tot} = \frac{C_{adh1} C_{adh2}}{C_{adh1} + C_{adh2}}.$$

An approximate expression of the capacitance $C_{adh1}$ reads $$C_{adh1} = \varepsilon_{adh}\varepsilon_0 \frac{A_{ring}}{l_{adh}}, \quad \text{Eqn. 2}$$

where $\varepsilon_{adh}$ is the relative effective dielectric constant of the adhesive, the foil and the top non-conductive layer of the skin, $\varepsilon_0$ is the vacuum permittivity, $A_{ring}$ is the area of the ring capacitor and $l_{adh}$ is the distance between the electrically conductive films and the conductive part of the skin. When a leak occurs e.g. from the centre of the bandage and outwards, the distance $l_{adh}$, between the top conductive films of the inner ring 7 and the conductive layer of the skin 25 increases, as shown in FIG. 1b. As a result, $C_{adh1}$ decreases, and according to Eqn. 1, $f_{res}$ increases. The present invention is therefore capable of detecting parts of the adhesive coming off the skin and voids or channels created before leakage of body fluid or faeces. Another advantage of the present invention is that enables detection of both leakages originating from the peripheral of the bandage and propagating towards the opening 3 and leakages originating from the opening 3 and towards the periphery.

On the other hand, the adhesive also absorbs water. The effective dielectric constant of the adhesive/foil is approximately $\varepsilon_{adh}\sim 2.5$, whilst the dielectric constant of water is as much as ~80 at DC, and somewhat smaller at higher frequencies. Therefore, as the adhesive absorbs water, according to Eqn. 2, $C_{adh1}$ increases, and according to Eqn. 1, $f_{res}$ decreases. As a consequence of this behaviour, by monitoring the resonance frequency as a function of time, a leakage can be discriminated against other changes induced by the environment, such as changes in temperature, a soaked adhesive due to sweat, mechanical stresses or other non-leakage induced sensor signals by analysing the temporal evolution of the resonance frequency.

The dimensions of the bandage illustrated in FIG. 1 may for a wound dressing be in the range of diameters or lengths from 5 mm to 500 mm, more preferably from 30 mm to 150 mm. For an ostomy bandage, the diameters or lengths may be in the range from 30 mm to 300 mm and more preferably from 50 mm to 150 mm. The periphery of the bandage may have various geometric forms such as circular, elliptical, rectangular, polygonal, or other forms. The electrically conductive pattern comprising coils and/or capacitor electrodes are not exclusively confined to spirals for the coils and circles for the capacitor electrodes as illustrated in the drawings. The coils may form any pattern of conductive leads with mutual electromagnetic coupling and any area of a conductive film with a closed or almost closed loop surrounding a stoma or a wound may form the electrode on a foil or an adhesive. Electrically conductive patterns also include patterns where the capacitor electrodes and the inductors are spatially distributed for example by means of a planar coil with a sufficiently broad wire width forming an electrode which achieves an appropriate capacitance to the conductive layer of the skin of a mammal. Appropriate capacitances mean that the resonance frequency according to Eqn. 1 matches suitable frequency bands for a reader unit and that it is not dominated by parasitic capacitances. The values of the capacitances and the inductances should thus match the frequency band chosen. For example, a typical value of the inductance is 10 μH, and a typical value of the combination of $C_{adh1}$ and $C_{adh2}$ is 20 pF yielding a resonance frequency of $f_{res}$=11 MHz according to Eqn. 1.

According to the present invention, the electrically conductive pattern surrounds the stoma or the wound and it can be designed in various sizes and shapes depending on the size and the shape of the stoma or wound. For a certain resonance frequency within a certain frequency band of the reader circuit, the dimensions of the electrically conductive pattern needs to be adapted to the frequency band. There are a number of parameters to tune in order to match a certain resonance frequency. The main parameters are the thickness of the adhesive ($l_{adh}$ in Eqn. 2), the area of the ring-capacitance electrode ($A_{ring}$ in Eqn. 2) and the number of wire turns (n) for the inductance, since in Eqn. 1 $L_c \propto$:n.

The conductivity of skin increases several orders of magnitude when the frequency changes from DC up to approximately 100 MHz and the difference between wet skin and dry skin becomes smaller, the higher the frequency (see e.g. V. Raicu et al. Phys. Med. Biol. 45 (2000) L1-L4). Lower frequencies may be preferred for immunity to parasitic effects and the ability to penetrate intervening material. Higher frequencies enhance measurement accuracy and make the sensor less sensitive to variations in skin humidity.

Standardized and suitable frequency bands for passive radio-frequency-identification-tags are for example 125 kHz-148 kHz, 13.56 MHz, 860-960 MHz, 2.45 GHz where the first two bands are based on inductively coupling, and the latter two bands are usually based on an electrical dipole coupling. The frequency band in the range from 5-20 MHz is most preferable, but other frequency bands can be employed for the present invention as well.

For a resonant circuit, there are a number of parameters that are affected when the electrical properties of a dielectric material is altered by an external condition, which in the present case is a leak. One parameter is the resonance frequency as mentioned above, where a response is measured sweeping an applied voltage over a certain frequency band and performing signal processing of the response as function of applied frequency.

Also the harmonic spectrum may be affected. In this case, detection may be carried out sweeping a receiver through a range of frequencies to characterise a harmonic spectrum. A third parameter is the quality-factor (Q-factor) of the circuit (modified by a change in electrical conductance), where the width of the resonance curve is measured or the response to an RF (Radio Frequency) burst and the ringing of the resonator is sensed between bursts.

Methods of measuring parameters in resonance circuits are described in e.g. U.S. Pat. No. 6,025,725.

It should be understood that for the two ring-electrodes of the present invention, the capacitance between each electrode and the conductive layer 25 of the skin of a mammal ($C_{adh1}$ and $C_{adh2}$) should dominate over the capacitance between the two ring-electrodes ($C_w$). As a consequence, a minimum distance (s) should be provided between the outer radius of the inner electrode ($r_2$) and the inner radius of the outer electrode ($r_3$). The quality factor Q may be limited by the finite conductance of the skin, and there is an upper limit on the ratio between s and the width (w) of any of the two ring-electrodes. The ratio $$\frac{s}{w}$$

is preferable within the interval:

$$1/50 < \frac{s}{w} < 20,$$

more preferable within $$1/10 < \frac{s}{w} < 5$$

and even more preferable within $$1/4 < \frac{s}{w} < 1.$$

The quality factor Q may also be limited by the finite conductance of the electrodes, which depending on the materials used puts a lower limit on the ratio between the height (h) of the electrodes and w. In practical production methods, the height of the electrodes may not be excessively large. The ratio $$\frac{h}{w}$$

is preferable:

$$10^{-6} < \frac{h}{w} < 10^{-1},$$

and more preferable $$10^{-4} < \frac{h}{w} < 10^{-2}.$$

Electrode materials may be metals like silver, gold, aluminium or copper or paste of silver or aluminium; conducting polymers like polyaniline, polypyrrole, ethylenedioxythiophene, poly(p-pyridyl vinylene); or amorphous conducting carbon films, films of conducting carbon fibres or polymer-conducting-carbon-black.

Figure 3:
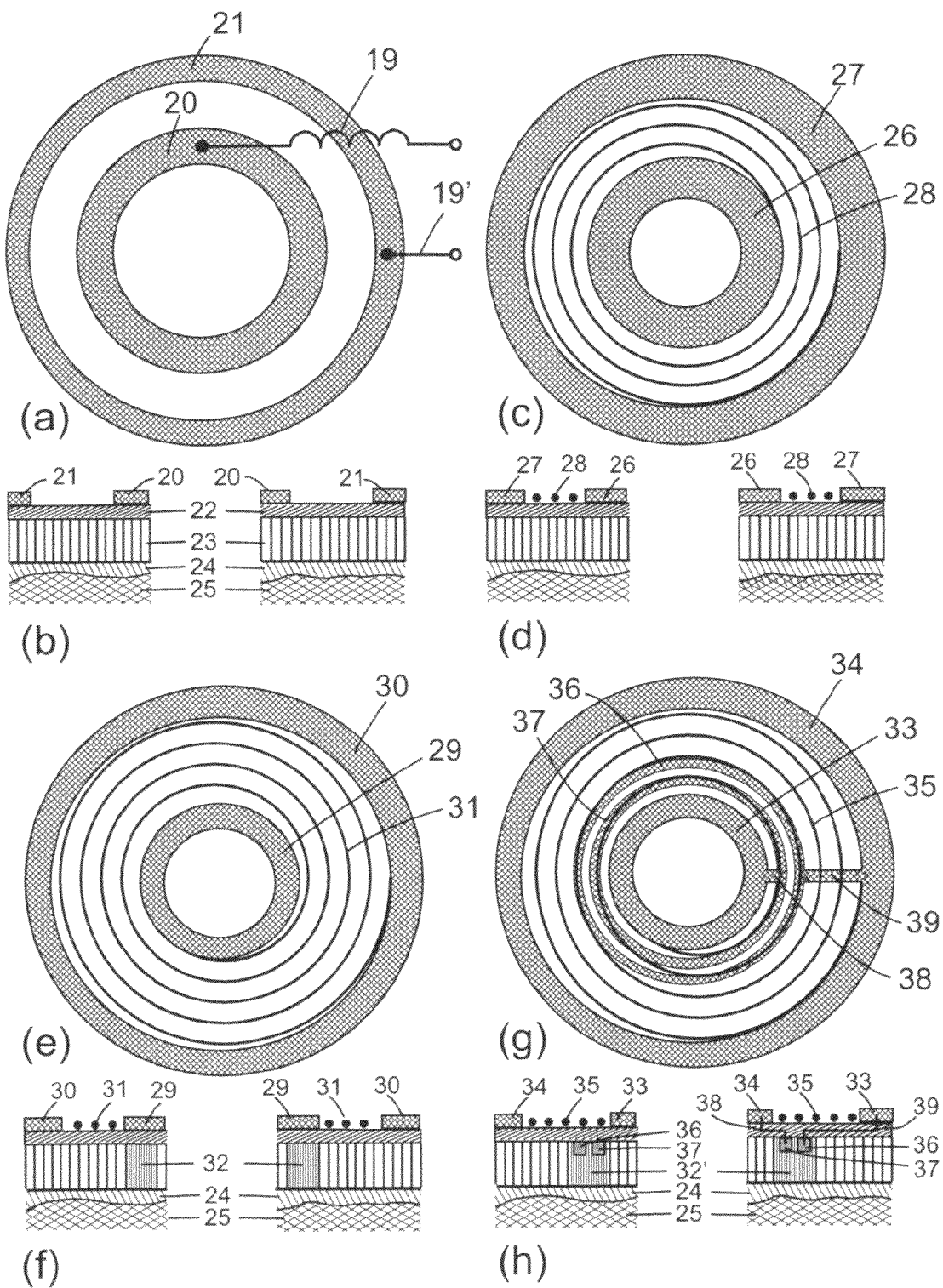
FIGS. 3a, 3b, 3c, 3d, 3e, 3f, 3g and 3h show four alternative embodiments of dressings according to the invention both in top views and in cross-sectional views.

FIGS. 3a-3h illustrate schematics of the electrically conductive film patterns and cross-sectional views of four different embodiments of the present invention with an adhesive 23 attached to the surface of the skin 24 of a mammal and a top-foil 22 on top of the adhesive. FIGS. 3a and 3b illustrate a pattern comprising two ring-capacitors 20 and 21 connected to a discrete inductor 19 forming a resonance circuit on the top-foil 22. FIGS. 3c and 3d illustrate a pattern comprising two ring-capacitors 26 and 27 and a planar coil 28 connecting the capacitors. FIGS. 3e and 3f illustrate a pattern comprising two ring-capacitors 29 and 30 and a planar coil 31 connecting the capacitors, but with part of the adhesive comprising a channel 32 guiding a leak to the vicinity of the inner ring-capacitor 29. The channel 32 may comprise a gap of air or a material with highly liquid guiding properties such as wet-table, hydrophilic fibrous materials. The liquid from an ostomy or from a wound has a high electrical conductivity and it increases the capacitive coupling between the inner conductive ring 29 and the conductive part of the skin 25. As a result, a change in the resonance frequency occurs, and the leak is detected, when it reaches the channel 32. The channel 32 may also act as a "leak stopper" providing a lag in a propagating leak.

The part of the adhesive comprising a channel 32 may alternatively guide a leak to the vicinity of the coil 31 and thereby increase the capacitive coupling between the coil 31 and the conductive layer of the skin 25 and between the coil and the electrode 29 and/or between the wires of the coil. The function of the leak-guiding channel 32 is to enhance the response sensitivity of the resonance circuit by increasing the resonance frequency shift, when a leak occurs.

FIGS. 3g and 3h illustrate an electrically conductive pattern comprising two ring-capacitors 33 and 34, a planar coil 35 connecting the capacitors and two additional conducting rings 36 and 37 connected in parallel to the ring-capacitors 33 and 34 by means of electrical connectors 38 and 39, respectively, where the two additional conducting rings are in contact with part of the adhesive in which a channel is formed 32' guiding the leak to be in proximity to the two conducting rings 36 and 37. The liquid from an ostomy or from a wound will form a capacitive or galvanic coupling between the two conducting rings 36 and 37. As a result, changes in the resonance frequency and/or the quality factor of the circuit occur, and the leak is detected when it reaches the channel 32'. The channel 32' may also act as a "leak stopper" providing a delay in a propagating leak. The channel 32' may comprise a gap of air or a material with highly liquid guiding properties such as wettable, hydrophilic fibrous materials. The fabrication of the two conducting rings 36 and 37 may be made using a folded foil enabling electrical connection from the top-side of the foil to the bottom side of the foil. Such methods of folding electrical circuits on foils are disclosed e.g. in U.S. Pat. No. 6,025,725.

FIGS. 4a-4d show partly in perspective and partly cross-sectional views of three different embodiments of the present invention with multi-layer adhesives and electrically conductive patterns. One embodiment is illustrated with a perspective view in FIG. 4a and a cross-sectional view in FIG. 4b, the multi-layers comprising a first adhesive 40 attached to the surface of the skin of a mammal 24, a first foil 41, a pattern comprising a set of two ring electrical electrodes 42 and 43 forming electrical connections to the wires 95 and 96, respectively, a second foil 41', a second adhesive or another material 45, a third foil 46, an electrically conducting shield layer 44, and a top foil 46'.

As illustrated, the extent of the foils 41 and 41' may be limited to an area covering the ring electrodes or they may be extended over the whole bandage. Similarly, the electrically conducting shield layer (44) may be extended over the whole bandage or, it may be bounded by an area sufficiently overlapping the area of the electrodes to prevent capacitive coupling from the environment above the top-foil 46'.

The first and the second foils isolate the electrically conductive films from the adhesive. When the adhesive 40 absorbs liquid, the foil prevents the liquid from getting into physical contact with and short-circuiting the electrically conductive films. The two foils 41 and 41' may be any electrically isolating layers. In applications, where the adhesive does not get soaked, they may not be needed. The two ring electrical electrodes 42 and 43 form capacitors with the conductive skin layer 25, $C_{adh1}$ and $C_{adh2}$, respectively and a capacitor to the electrically conducting shield layer 44, $C_w$, which approximately can be expressed as a series connection of two ring-capacitors $$C_w = \varepsilon_{adhtop}\varepsilon_0 \frac{1}{t_{adhtop} + t_{foil}} \frac{(r_2^2 - r_1^2)(r_4^2 - r_3^2)}{r_2^2 - r_1^2 + r_4^2 - r_3^2}. \quad \text{Eqn. (3)}$$

In Eqn. 3, $\varepsilon_{adhtop}$ is the effective dielectric constant of the top adhesive and the second and third foil, $t_{adhtop}$ and $t_{foil}$ are the thickness of the second adhesive and the third foil, respectively; $r_1$ is the inner radius of the inner conductive ring 43, $r_2$ is the outer radius of the inner conductive ring, $r_3$ is the inner radius of the outer conductive ring, and $r_4$ is the outer radius of the outer conductive ring. The total capacitance seen from the two wires 95 and 96 is given by $C_w$ in parallel with the series connection of $C_{adh1}$ and $C_{adh2}$ (see FIG. 2b).

Examples of dimensions of a typical design of a leak sensor integrated on an ostomy base plate are as follows. The relative effective dielectric constant of the adhesives, the foils and the top non-conductive layer of the skin, $\varepsilon_{adh}=\varepsilon_{adhtop}=2.5$, thickness of adhesive layer 40, $t_{adh}=0.7$ mm, thickness of adhesive layer 45, $t_{adhtop}=0.3$ mm, thickness of third foil, $t_{foil}=0.1$ mm, the radii of the conductive rings, $r_1=26$ mm, $r_2=30$ mm, $r_3=33$ mm, $r_4=36$ mm, the total resistance of the skin for the current flowing in the skin between the inner ring-capacitance and the outer ring-capacitance, $R_{skin1}+R_{skin2}=68\ \Omega$, series resistance of the top conductive layer 44, $R_s=10\ \Omega$. Using a total capacitance of $$C_{tot} = C_w + \frac{C_{adh1} C_{adh2}}{C_{adh1} + C_{adh2}},$$

and an inductance of $L_C=4.7\ \mu H$ yields according to Eqn. 1 a resonance frequency of $f_{res}=13.56$ MHz, and a quality factor of $Q=f_{res}/\Delta f=9.7$, with $\Delta f$ being the full-width-half-maximum of the resonance curve. In practice, it is necessary to take account of parasitic capacitances and the leak sensor design needs to be adjusted accordingly. Considering the teachings above such adjustments would be known to a person skilled in the art.

A leak with an initial air channel of width, height and length of $w_{chan}=8$ mm, $h_{chan}=1$ mm, and $l_{chan}=4$ mm, respectively, exhibits a change in $C_{adh1}$ of $\Delta C_{adh1}=-0.8$ pF corresponding to a change in resonance frequency of $\Delta f_{res}=+0.04$ MHz. This is a typical measured value of change in resonance for an observed leak. However, early detection of a leak often requires measurements of smaller signal changes. In the art, using a pulse-like excitation signal and a microcontroller-based circuit, measurements of changes in resonances for resonance-based sensors have been reported to 0.001% achieved in approximately 40 ms [K. Zeng et al., Rev. Sci. Instrum. Vol. 73 (2002), p. 4375]. For the present example of a leak sensor, an accuracy of this magnitude corresponds to a measurable change in frequency of 0.0001 MHz, a number, which is a factor of 400 smaller than the leak induced change in resonance frequency as mentioned in the present example.

In practice, the measurement accuracy of the present invention of a leak sensor is not limited by the signal to noise ratio, but rather by influence of externally induced signal changes. In order to reduce such influences, an electrically conducting shield layer 44 has been introduced in the embodiment as illustrated in FIGS. 4a-4b. The shield layer eliminates capacitive coupling between the environment above the top-foil and the electrical conductors 42 and 43. In ostomy applications, such environmental disturbances could be provided by the highly conducting liquid in an ostomy bag.

FIGS. 4*c* and 4*d* show alternative embodiments with compensation for effects of environmental disturbances in the determination of the resonance frequency. In FIG. 4*c* the multi-layers comprise a first adhesive 47 attached to the outer skin of a mammal 24, a first foil 48, a first electrically conductive pattern comprising two ring-electrodes 49 and 50 and a first planar coil 51 electrically connecting the electrodes, a second foil 48', a second adhesive or another material 53 and a second foil 52 with a second electrically conductive pattern on the foil comprising a second set of two ring-electrodes 54 and 55 and a second planar coil 56 electrically connecting the second set of electrodes.

In this embodiment of the invention, the first set of electrically conducting patterns 49, 50 and 51 is employed to detect a leak propagating at the interface between the surface of the skin 24 and the first adhesive 47. The second set of electrically conductive patterns 54, 55 and 56 is employed to monitor disturbances from the environment and subtracting this contribution from the response of the first resonance circuit 49, 50 and 51. This method enables discriminating between a leak and an environmental disturbance.

There is some mutual inductive and capacitive coupling between the two resonance circuits, which should be taken into account as known by a person skilled in the art.

In FIG. 4*d*, the multi-layers comprise a first adhesive 67 attached to the surface of an outer skin of a mammal 24, a first foil 57, a first electrically conductive pattern comprising two ring-electrodes 58 and 59 and a planar coil 60 electrically connecting the rings, with part of the adhesive comprising a channel 66 guiding a leak to the vicinity of the inner ring-electrode 59, a second foil 57', a second adhesive or another material 61 and a top-foil 62 with a second electrically conductive pattern comprising a second set of two ring-electrodes 63 and 64 and a second planar coil 65 electrically connecting the second set of electrodes.

Figure 4:
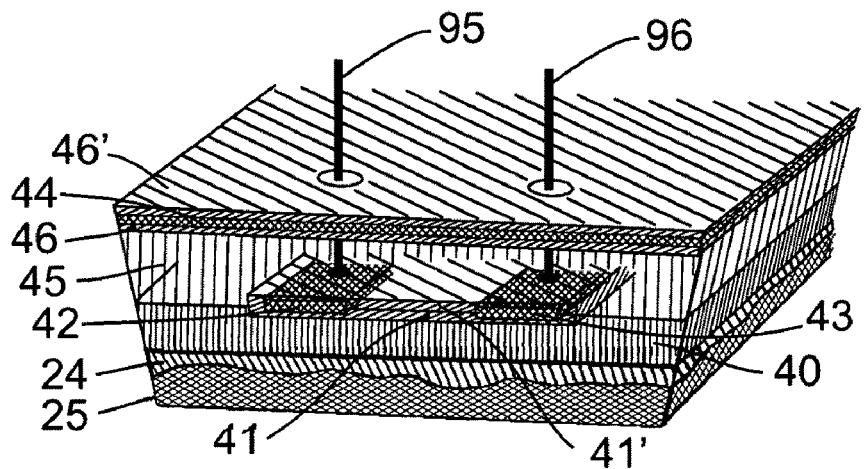
FIGS. 4a, 4b, 4c and 4d show even further alternative embodiments of dressings according to the present invention.
Figure 4:
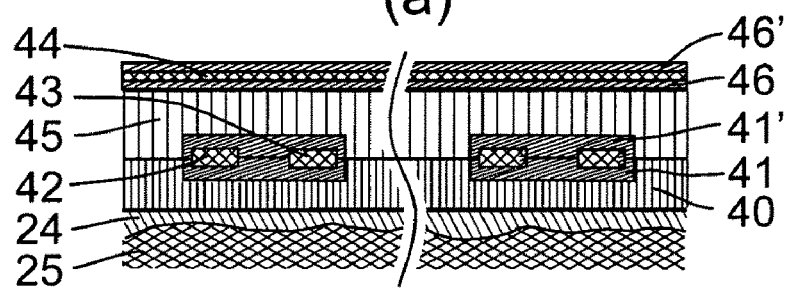
Figure 4:
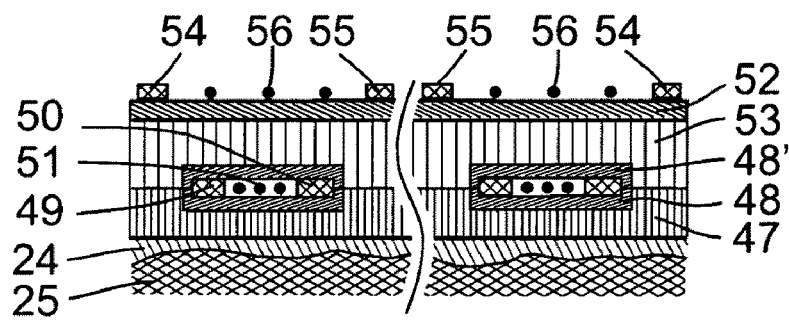
Figure 4:
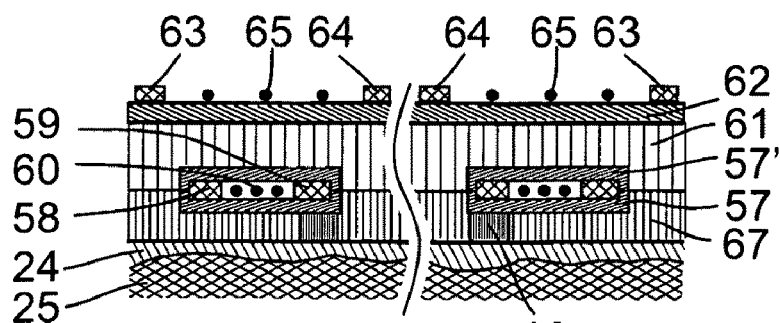
Figure 5:
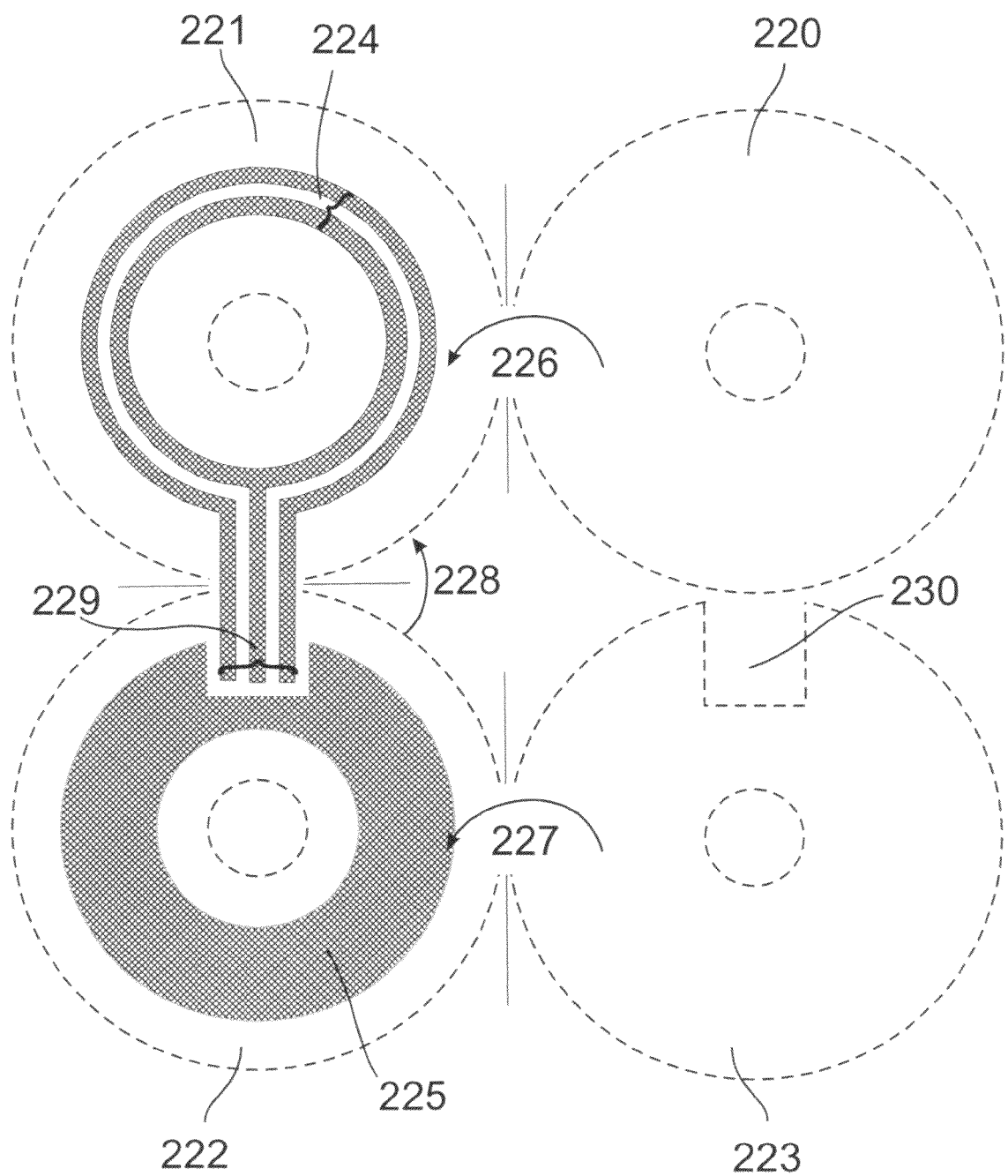
FIG. 5 shows an alternative embodiment of a foldable electrical circuit suitable to be disposed on a standard ostomy base plate.

FIG. 5 illustrates another approach of contacting an electrically conductive pattern embedded in an adhesive as illustrated in FIG. 4*a*. FIG. 5 illustrates schematically a piece of foil or the like which may cut along the dashed curves and be folded to make first, second, third and fourth sections 220, 221, 222 and 223 overlap each other in four layers. The second section 221 has an electrically conductive pattern of two ring-electrodes 224 and the third section 222 has an electrically conducting shield 225 having an outer radius greater than the two ring-electrodes and an inner radius less than the inner radius of any of the two ring-electrodes. Electrical contacts to the two ring-electrodes on the third section 222 may be made by means of the conductive strips 229 from the second section 221.

For the fabrication of the multi-layer sensor, the sections are folded as follows, where it should be understood that the printed pattern illustrated in FIG. 5 is on the side referred to as the front and the opposite side of the sheet is referred to as the back. In the first step, the first section 220 is folded along a first folding line 226, between the first and second section, where the front of the first section 220 is folded onto the front of the second section 221. In the second step, the fourth section 223 is folded along a second folding line 227, between the third and fourth section, where the front of the fourth section 223 is folded onto the front of the third section 222. Finally, the third and fourth section 222 and 223 are folded along a third folding line 228, between the second and third section, where the back of the third section 222 is folded onto the back of the second section 221. An adhesive or another dielectric material preferably with high flexibility is optionally disposed on the back of either the second or third section 221 and 222. The multi-layer structure may then be attached to an adhesive of a dressing or a bandage. In the folded configuration, the cut-out 230 provides means for allowing galvanic contact to the electrodes of a reader (as will be described later), which may be placed on the cut-out. Alternatively, employing capacitive coupling to the reader the cut-out 230 may be avoided.

Rather than using one piece of foil, other embodiments also include configurations where the second and third sections 221 and 222 are formed as one layer and the first and fourth sections 220 and 223 are formed as two separate layers. Other embodiments may also include configurations, where the second and third sections 221 and 222 are laminated together with one layer comprising first and fourth sections 220 and 223 and configurations where the first section 220 is a layer coated on the third section 221, and the fourth section 230 is a layer coated on the third section 222. The coating may be performed using techniques such as spin-coating, vacuum coating or spray-coating.

Figure 6:
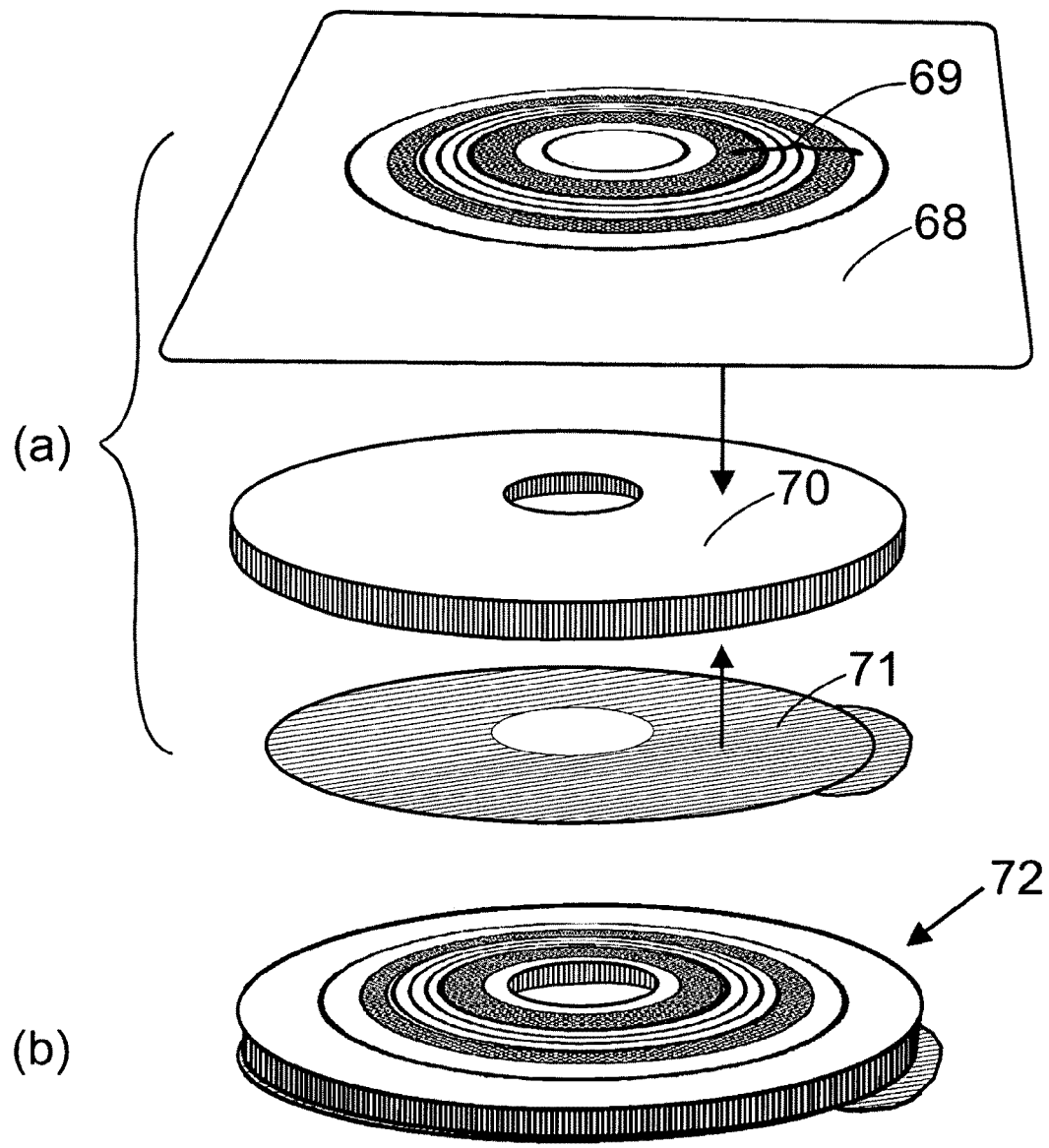
FIGS. 6a and 6b show an alternative embodiment of a dressing according to the invention in an exploded and assembled perspective view, respectively.

FIGS. 6*a* and 6*b* illustrates a method of fabricating a leak sensor. FIG. 6*a* illustrates the bandage produced comprising the three components: a top-foil 68 comprising an electrically conductive pattern 69, a middle component of an adhesive 70 and a bottom component of a release liner 71. In FIG. 6*b* the top foil and the adhesive have been welded together by heat or another suitable welding method.

This method may also be used to produce configurations such as illustrated in FIG. 4 with multiple layers of foils and adhesives.

The present invention also covers a top-foil comprising a two-dimensional array of electrically conductive patterns, the two-dimensional array being transferred to a series of bandages separated by appropriate cutting. The electrically conductive patterns may be made by, but not limited to, methods such as screen-printing or tampon printing using silver paste or aluminium paste, or inkjet-produced patterns of solid copper, which may be made by a system like the PRECO Metal-Jet 6000. In addition to the resonance circuit, other electrical components may also be printed on the foil 68 like an RF antenna or a microwave antenna.

The method of the present invention of fabricating a sensor on a foil attached to an adhesive is compatible with existing processes in the production of ostomy bandages, base plates and wound dressings. Therefore the method allows for low cost implementation, which is simple and suitable for mass-production.

The foil comprising the sensor circuit with the electrically conductive patterns may be produced with an adhesive on the backside and attached to a release liner. The user removes the release liner and attaches the foil comprising the sensor circuit to the top of the ostomy bandage or wound dressing. Such a sensor provides flexibility for the user, since it can be attached to a number of different products, not limited to particular ostomy bandages or wound dressings.

Figure 7:
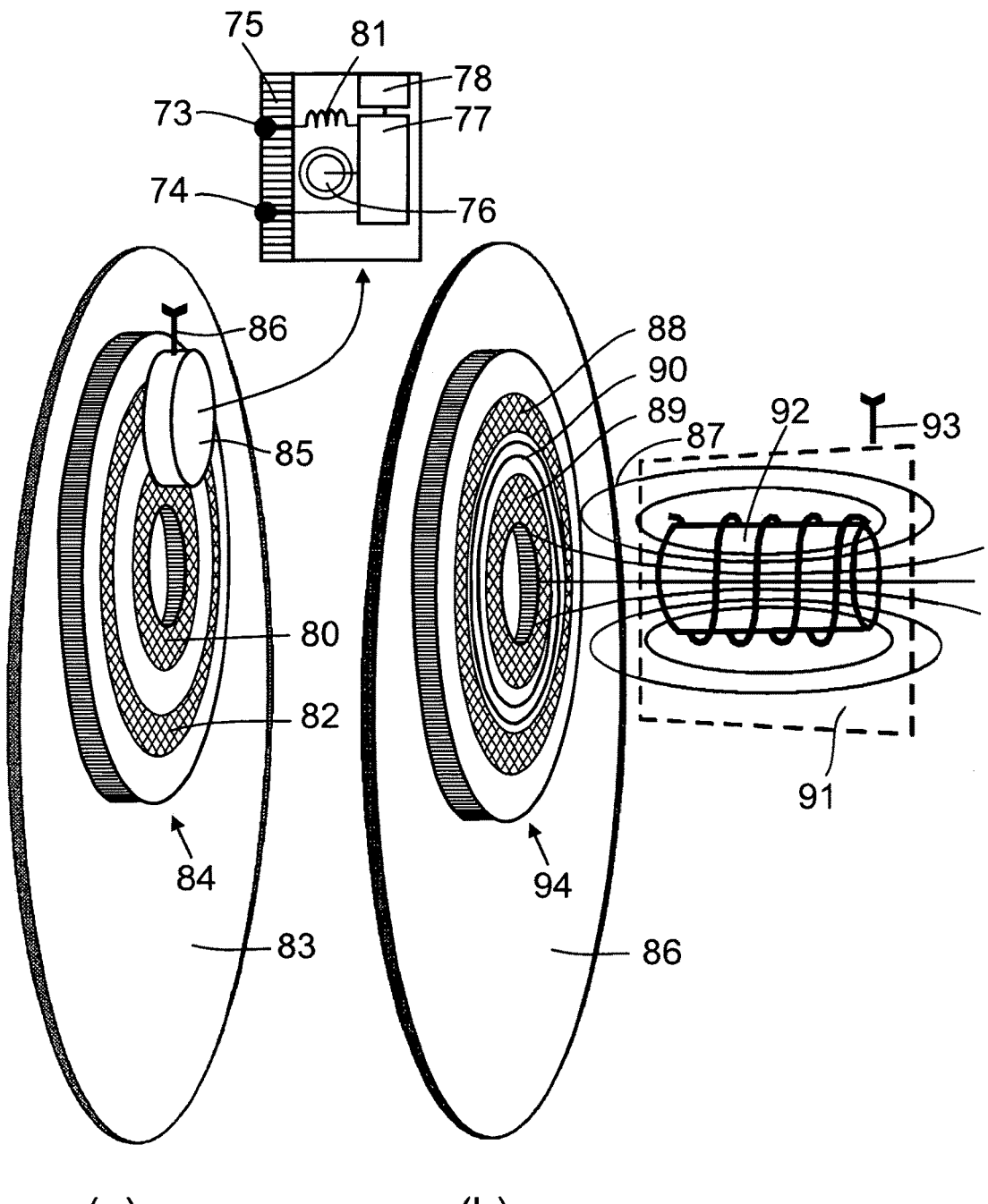
FIGS. 7a and 7b show two different embodiments of reader units suitable for detecting changes in capacitance according to the present invention.

FIGS. 7*a* and 7*b* illustrates two embodiments of the present invention regarding the coupling to a leak sensor integrated in a bandage of an adhesive 84 of an ostomy bag 83. In FIG. 7*a*, the reader unit 85 couples via wires 73 and 74 to the electrically conductive pattern comprising an inner ring-electrode 80, and an outer ring-electrode 82. The coupling may be galvanic, capacitive or inductive. The wires 73 and 74 are attached to the electrically conductive pattern preferably by means of a second adhesive 75. A coil 81 is preferably included in the reader unit. Which connected in series or parallel with the two ring-electrodes constitutes an electric resonance circuit (see FIG. 3*a*). The reader unit comprises a battery or any other kind of energy source 76, a modulation and demodulation circuit transmitting and receiving electrical signals to and from the electrically conductive pattern combined with a micro-controller with firmware processing the data 77 and a data communication unit and drivers for an antenna, LEDs, vibrators or the like 78.

Once the user puts the reader unit onto the bandage 84, the reader makes an Initial measurement of the resonance frequency. The reader unit may have a button that the user presses, when he/she mounts the reader unit, or more preferably the reader unit starts automatically searching for a resonance frequency, when it has been detached from an ostomy bandage for example because the user has changed his/her bag. Once the reader unit has found the resonance frequency, it waits a few minutes in order to let temperature and humidity conditions stabilize. When the resonance frequency has stabilized, it uses the value of the resonance frequency as a reference frequency and keeps measuring the resonance frequency.

When the difference between the resonance frequency measured and a preset value exceeds a threshold or exhibits a characteristic temporal pattern associated with a leak, the reader unit 85 sends an alarm, either as an acoustic signal, a vibrating signal, a light signal such as a flashing LED or sends a wireless signal via the antenna 86 to an event handling device in a communication network such as a cellular telephone, a personal digital assistant, an iPod, a laptop or a PC. The wireless signal may be based on short-range communication standards like Bluetooth, Zigbee or WLAN or any suitable industrial, scientific, medical bands. The reader unit can be reused, when the user changes the ostomy bag. In another embodiment, the antenna 86 may be printed onto the top-foil of the adhesive. The present invention also includes embodiments where the coil 81 is avoided and the reader measures a change in capacitance rather than a change in resonance frequency (see the following description of FIG. 13).

FIG. 7b illustrates another embodiment of the present invention, where the reader unit 91 comprises an inductive coupling to the coil 90 of the resonance circuit. The reader unit may include a frequency sweeping circuit and measures the resonance frequency from the frequency dependent coupled impedance. Determination of resonance frequency is well known in the art; see e.g. O. Akar et al. Sensors and Actuators A95 (2001) 29-38). US patent application 2003/0169032 describes some methods and circuit configurations in determining the resonance frequency based on the frequency domain. K. Zeng et al. *Rev. Sci. Inst Vol.* 73 (2002), p. 4375, describe a method and a circuit configuration based on the time domain. Methods of wireless detection are also known in the art and they are described e.g. in K. G. Ong et al. *Sens. Act. Vol. A*93 (2001), p. 33.

When the difference between the resonance frequency measured and a preset value exceeds a threshold or exhibits a characteristic temporal pattern, the reader unit sends an alarm, either as an acoustic signal, a vibration, a light signal such as a flashing LED or sends a wireless signal to a handling device in a communication network such as a cellular telephone a personal digital assistant, an ipod, a laptop, a PC or the like.

Similarly to the reader unit 85 in FIG. 7a, the reader unit 91 in FIG. 7b comprises a battery or any other kind of energy source, a modulation and demodulation circuit combined with a micro-controller with firmware processing the data and a data communication unit and drivers for antenna, LEDs, vibrators or the like.

Figure 8:
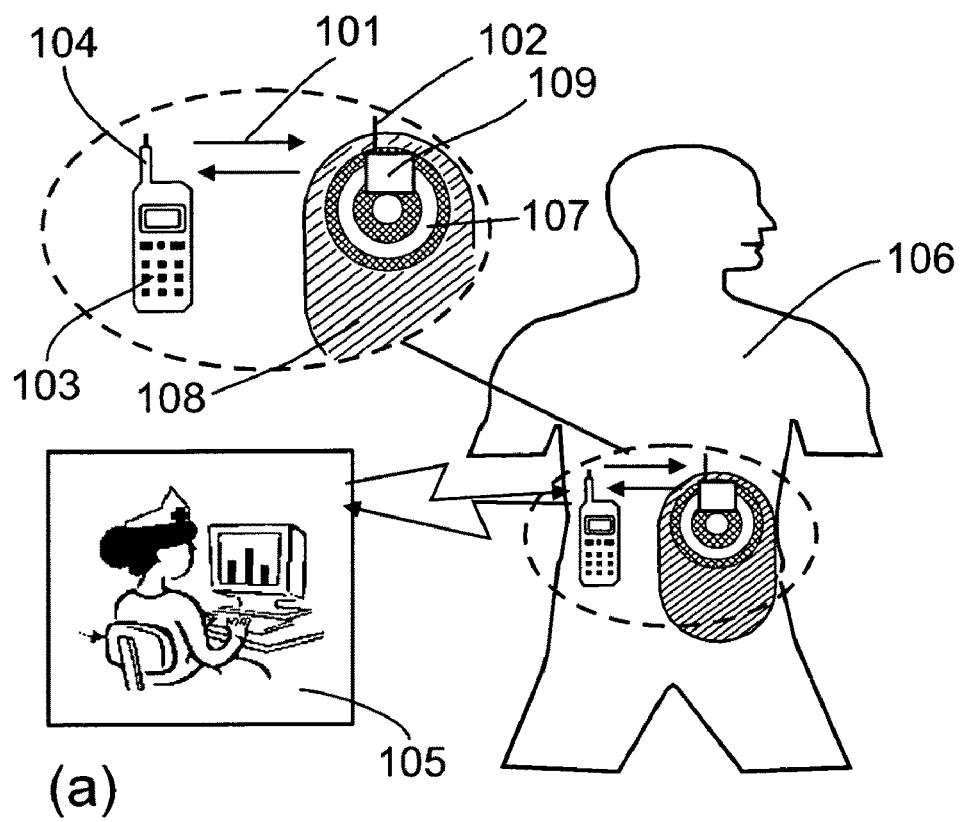
FIGS. 8a and 8b shows two different embodiments of a communication system for providing remote monitoring of a dressing according to the invention.
Figure 8:
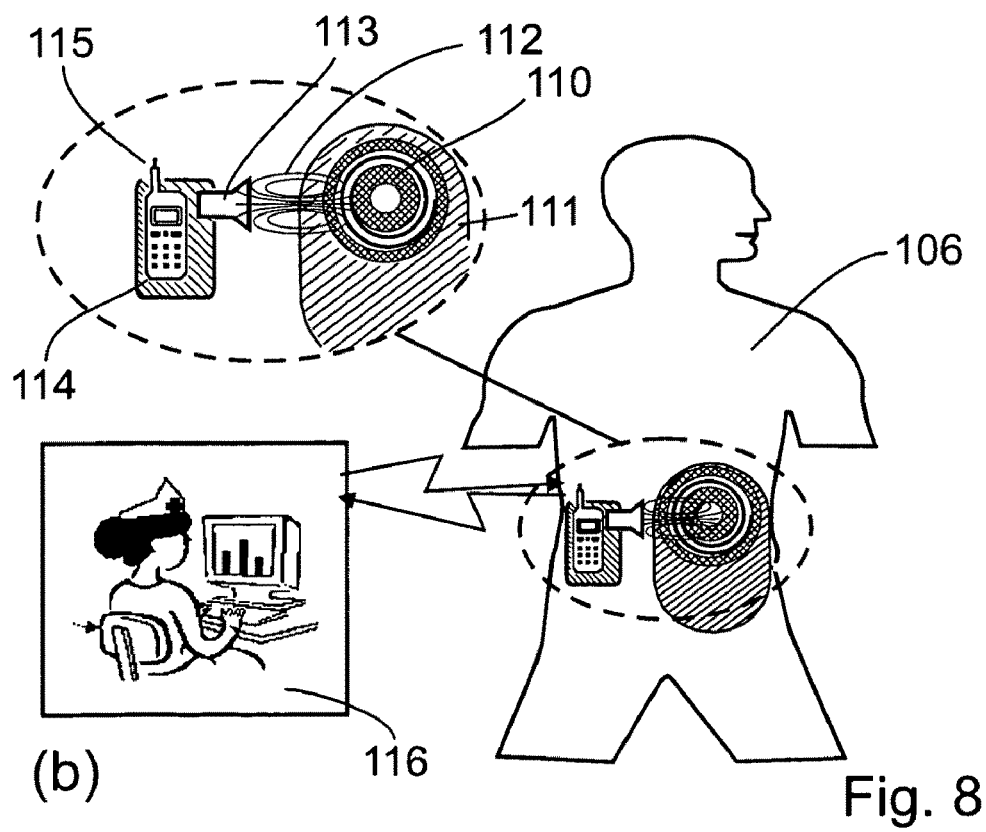

FIGS. 8a and 8b illustrates two methods of transmitting information about leak detection from the leak sensor to a service centre or a nurse. In FIG. 8a, the method is based on the sensor configuration in FIG. 7a. A leak detected by the reader 109 transmits the signal to an event-handling device 103 using short-range wireless communication. The handling device 103 may activate an alarm alerting the user by means of an acoustic signal, a vibration or the like. The event-handling device 103 transfers the signal to a service centre, where a nurse or other health caring personnel is requested to change a bandage or a dressing on a person. The event-handling device may be a cellular telephone, a personal digital assistant, a laptop, a PC or the like. The signal transfer to a service centre is carried out by GSM, GPRS, EGSM or DCS or it may be transferred through an intranet or the Internet.

In FIG. 8b, the method is based on the sensor configuration in FIG. 7b. The wireless detection of a leak by the reader 113 is transmitted to a service centre 116, where a nurse or other health caring personnel is requested to help the person to change a bandage or a dressing. The reader unit comprises an event-handling device 114 and transfers the signal directly to a service centre 116 or via a network to the service centre. The communication may be short-range through Bluetooth, Zigbee or WLAN or it may be long range such as GSM, GPRS, EGSM or DCS. The handling device 115 may activate an alarm alerting the user by means of an acoustic signal, a vibration or the like.

EXAMPLE 1

Figure 9:
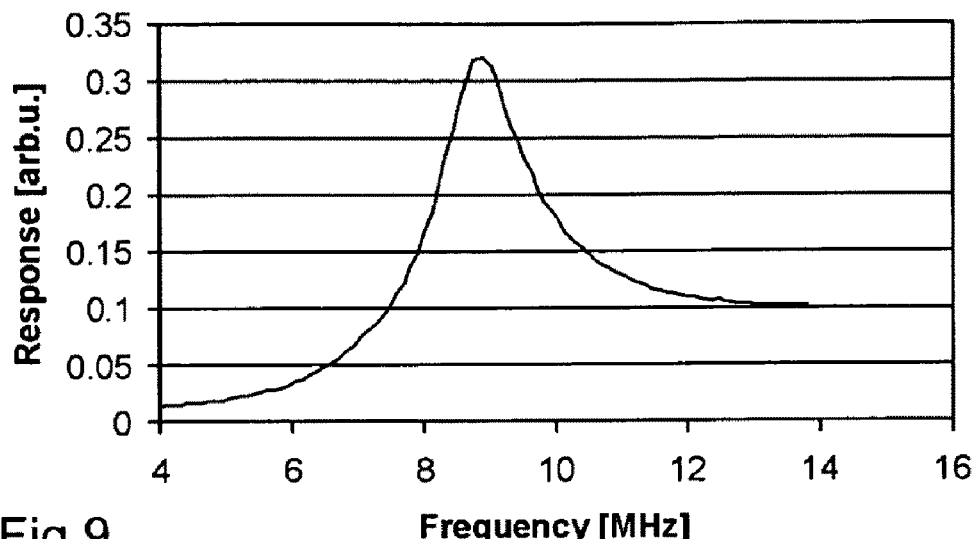
FIG. 9 shows a plot of an electrical response as a function of frequency for an embodiment of the present invention attached to the skin of a person.
Figure 10:
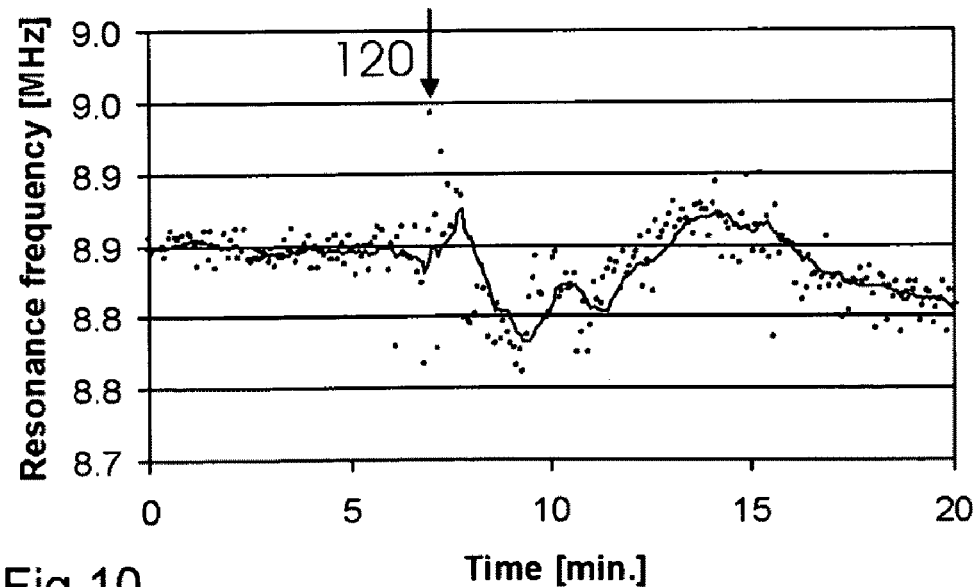
FIG. 10 shows a plot of the resonance frequency as function of time for an embodiment of the present invention attached to the skin of a person.

In example 1 the sensor response of a leak sensor for an adhesive of an ostomy bag with the adhesive attached to the skin of a person is determined when a leak is occurs. The leak sensor comprises an electrically conductive pattern of two ring-electrodes on a top foil of a bandage and welded to an ostomy bag filled with 0.9% NaCl aqueous solution simulating body liquid. The configuration is illustrated in FIG. 3a. The electrically conductive pattern is connected to an external coil of 4.7 µH and a sine-wave function generator sweeps the frequency from 4 to 14 MHz. FIG. 9 shows a plot of an electrical response (voltage across the external coil) as function of frequency and FIG. 10 shows a plot of the resonance frequency as function of time, when a leak occurs between the adhesive and the skin of a person at the point of time indicated by an arrow 120. From resonance curves acquired with a sample frequency of 0.1 Hz, the resonance frequency has been determined using a first-momentum fitting algorithm (see eg. C. Thirstrup and W. Zong, Sens. Act. B: Chemical, Vol. 106 (2005), pp. 796-802). The RMS noise of the data is 0.007 MHz corresponding to accuracy in the determination of the resonance frequency of 0.08%.

EXAMPLE 2

Figure 11:
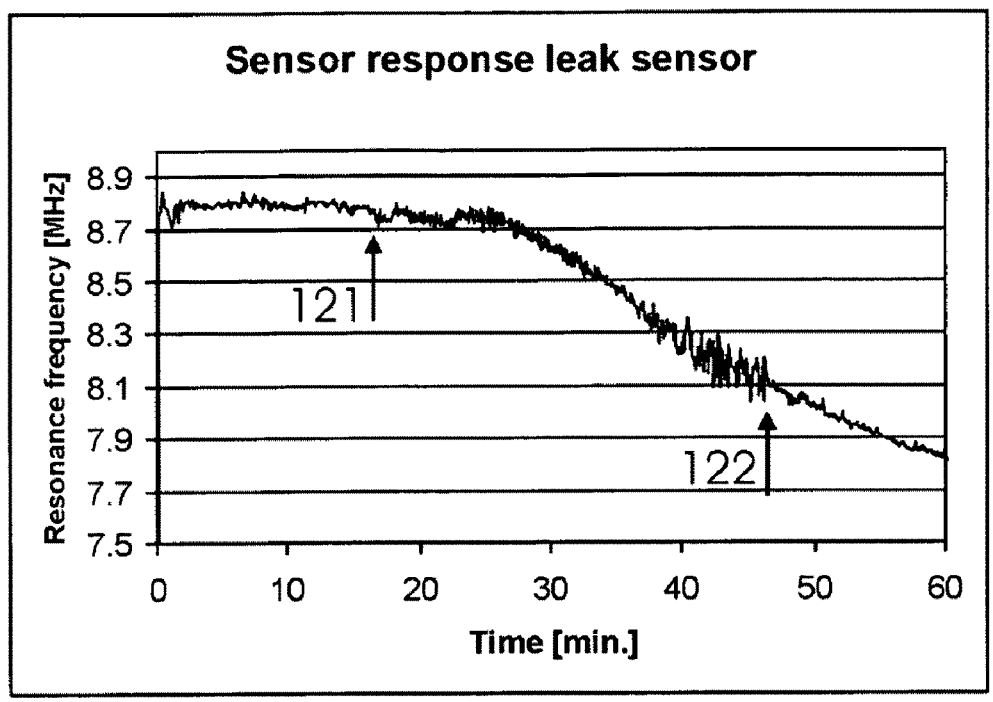
FIG. 11 shows a plot of the resonance frequency as a function of time for an embodiment of the present invention attached to the skin of a person.

In example 2, a sensor response of a leak sensor for an ostomy bag with an adhesive attached to the skin of a person is determined when the adhesive absorbs moisture. The leak sensor comprises an electrically conductive pattern of two ring-capacitors on a top-foil of a bandage and welded to an ostomy bag. The configuration is illustrated in FIG. 3a. In FIG. 11, the resonance frequency is plotted as function of time when the adhesive absorbs sweat from the skin of a cycling person. At the point of time 121, the person starts cycling from rest with 74 rotations-per-minute and at the point of time 122, the person stops cycling and rests. The resonance frequency has been determined using the method described in Example 1. Note that the sensor response to an adhesive absorbing sweat from a person is different from the response from a leak (see Example 1). The present invention can therefore discriminate between leaks and soaked adhesives.

EXAMPLE 3

Figure 12:
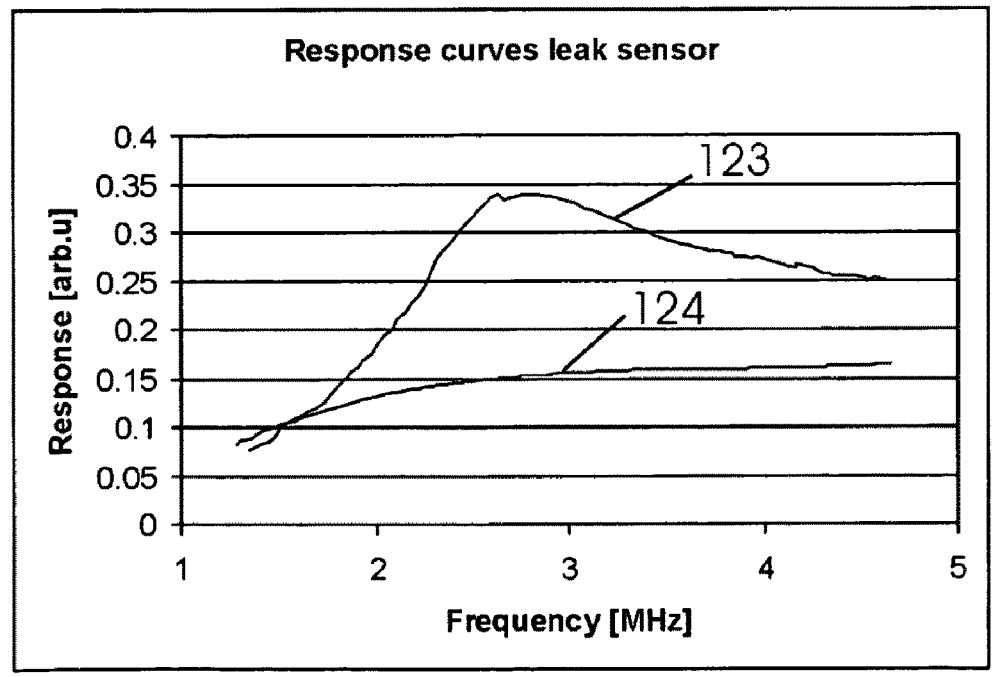
FIG. 12 shows a plot of the response before the occurrence of the leak and a plot of the curve after the occurrence of the leak for another embodiment of the present invention attached to the skin of a person.

In example 3, the sensor response is detected of a leak sensor based on two rings connected in parallel to the coil of an electrical resonance circuit with a top foil of a bandage welded to an ostomy bag filled with 0.9% NaCl aqueous solution simulating body liquid. The sensor is electrically connected to a sine-wave function generator sweeping the frequency from 1.4-4.6 MHz. The sensor configuration is illustrated in FIG. 3d apart from the fact that an external coil replaces the planar coil and that the two ring wires 36 and 37 in this example are touching the surface of the skin 24. In FIG. 12, the curve 123 is the response before occurrence of the leak and the curve 124 is after occurrence of the leak.

EXAMPLE 4

Figure 14A:
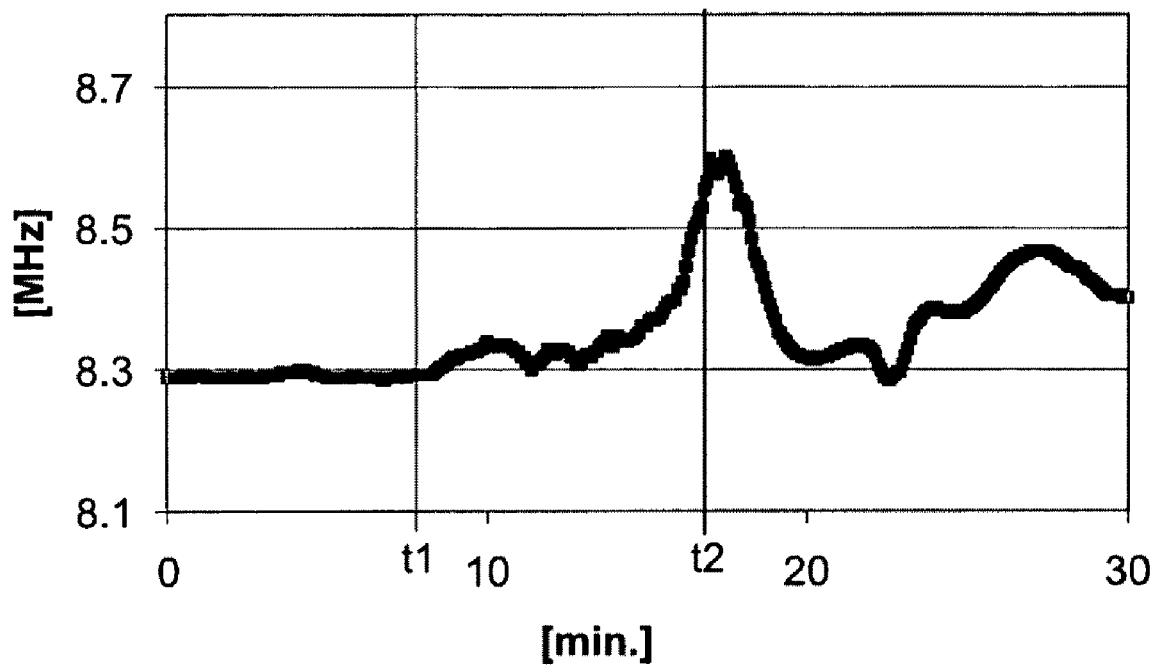
FIGS. 14a and 14b show a plot indicating a leak as illustrated by the resonance frequency as function of time for two different embodiments, respectively, of a dressing according to the invention attached to the skin of a person.

Further testing has confirmed the utility of the method and apparatus and shows a high reliability. FIG. 14a shows a curve plotted using data from a set-up comprising a configuration as shown in FIG. 3(a). The curve is a plot of the resonance frequency (MHz) as a function of time (min). A person wearing the set-up starts exercising after 8 minutes (t1), provoking a leakage, and after 17 minutes (t2) leakage is observed. As can be seen from the plot a considerable change in the resonance frequency occurs at t2.

EXAMPLE 5

Figure 14B:
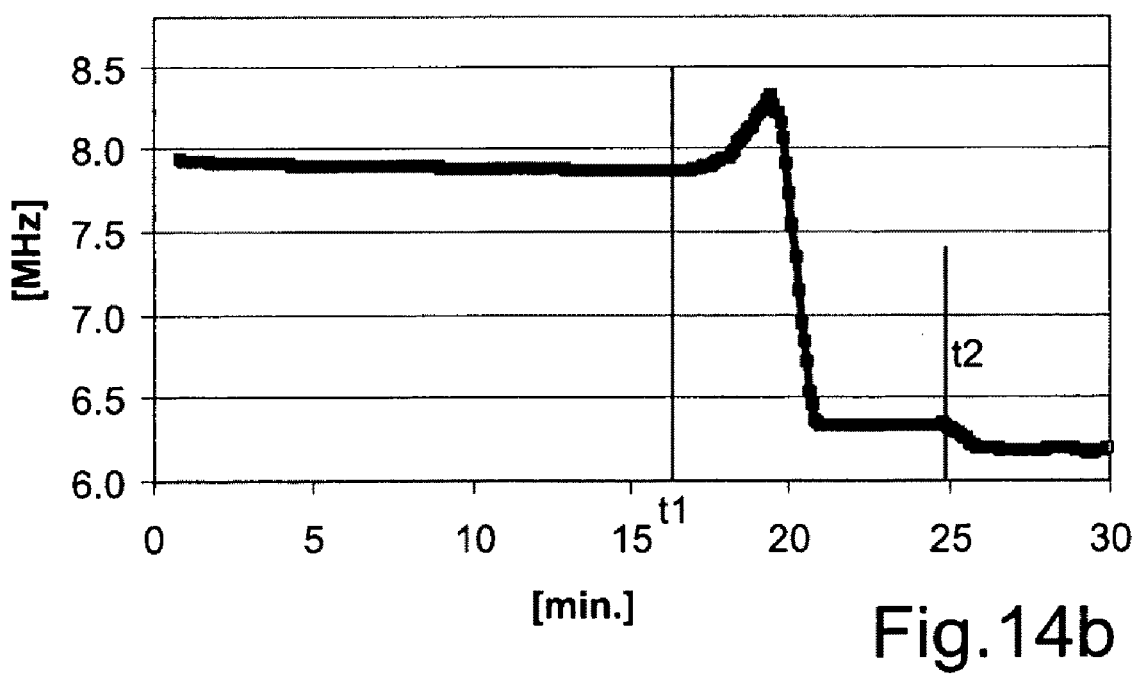

In another set-up using a sensor almost similar to that shown in FIG. 3(f), except that an external coil has replaced the integrated planar coil connected to the inner ring capacitance, data obtained have been plotted in FIG. 14b. The plot also shows the resonance frequency (MHz) as a function of time (min). In this set-up the start of provoking a leakage (t1) is begun after 16 minutes where a person wearing the bandage begins to exercise. A leakage is observed (t2) after 25 minutes. The considerable change in resonance frequency occurring between t1 and t2 (in particular between 19 and 20 minutes) is due to the filling of fluid in the channel 32 in FIG. 3(f). Although, at this time leakage travelling all the way through the bandage has not yet occurred. It is thus possible to obtain a significant indication that a leakage soon is created and thereby alert the user or caring nurse in due time.

Figure 13A:
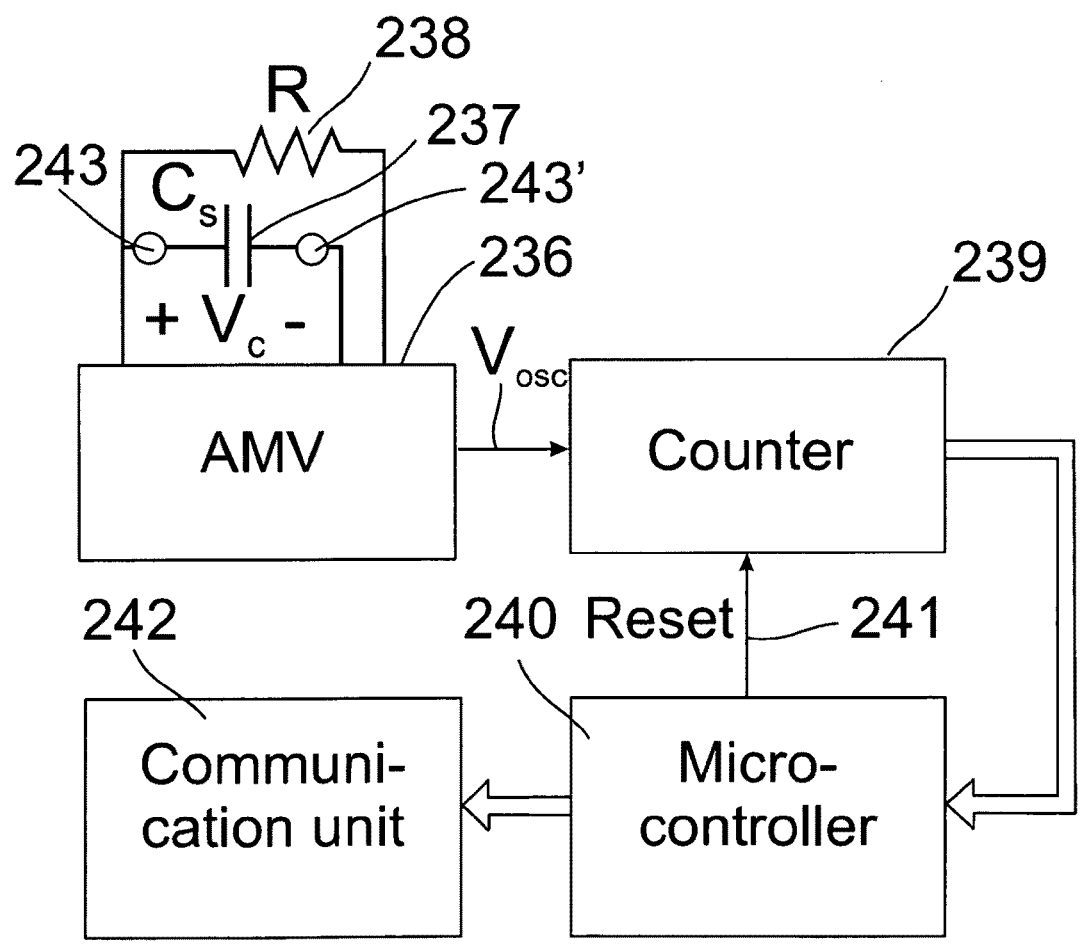
FIGS. 13a, 13b and 13c show an electrical block diagram and drawings of another embodiment of an electrical circuit applicable for the present invention.
Figure 13B:
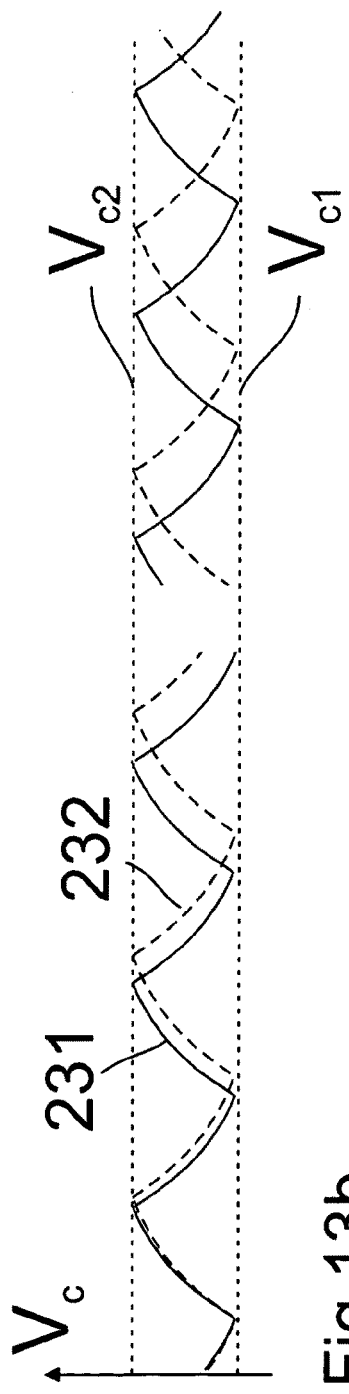
Figure 13C:
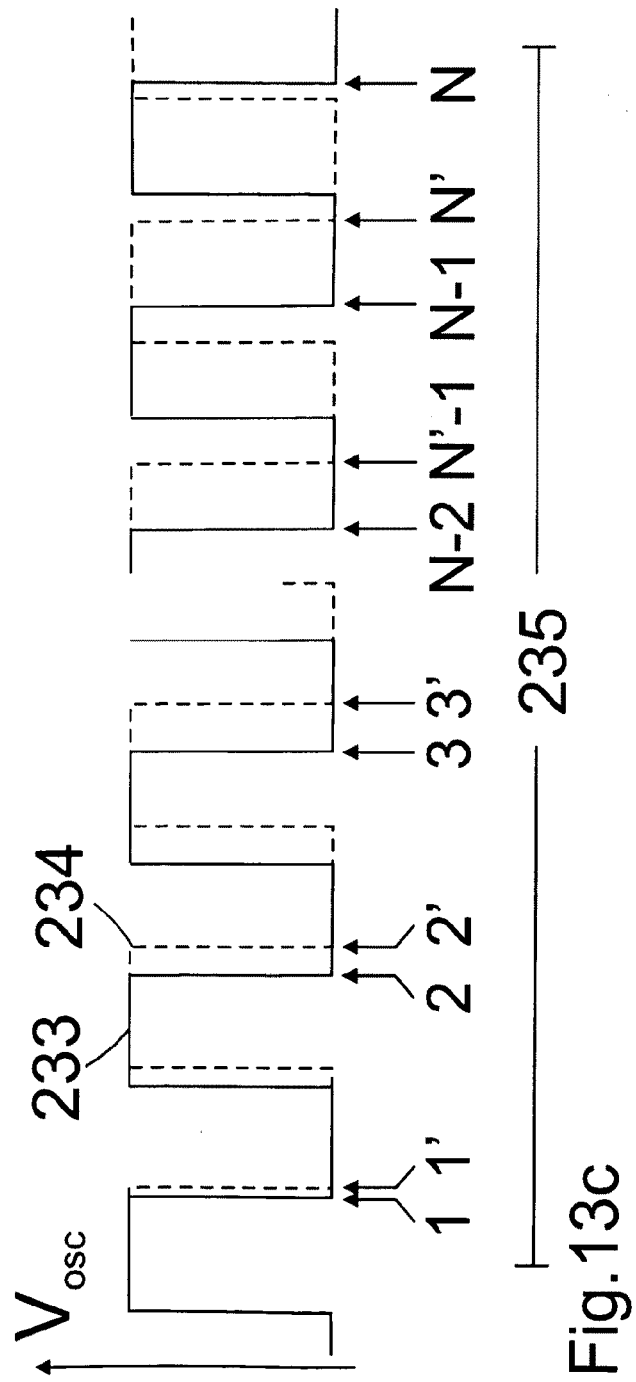

FIG. 13a illustrates an embodiment of electrical circuit blocks in the shape of a reader configuration comprising an astable multivibrator (AMV), which is an electrical component known by a person skilled in the art. FIGS. 13b and 13c show schematically the variation in the voltages across the capacitance of the sensor $C_s$ ($V_c$) and the output of the AMV ($V_{osc}$) as function of time. The reader configuration is based on measuring capacitance change from a change in the time constant of a resistor-capacitor (R $C_s$) circuit. The capacitor $C_s$ 237 of the sensor of the present invention and an external resistor R 238 are connected to the AMV 236. The capacitor may have a design as illustrated schematically in FIG. 3a or FIG. 4a, but in this embodiment the inductor is not needed. The reader may be attached to a leak sensor of an ostomy bag as depicted in FIG. 7a. As illustrated schematically in FIG. 13b, the sensor capacitor is periodically charging up and charging down with a voltage $V_c$ changing between two threshold values $V_{c1}$ and $V_{c2}$, respectively. When $V_c$ reaches $V_{c1}$, the output of the AMV ($V_{osc}$) goes high, and when $V_c$ reaches $V_{c2}$, $V_{osc}$ goes low, which is illustrated schematically in FIG. 13c. The AMV exhibits a square output signal $V_{osc}$ oscillating with a frequency (f), which is inversely proportional to the product of the capacitor and the resistor, i.e.

$$f \cong A \frac{1}{RC_s}, \qquad \text{Eqn. (4)}$$

with A being a constant.

When $C_s$ of the sensor changes, the time of charging up and charging down the capacitor changes, and the frequency of the output of the AMV changes according to Eqn. (4). For an increase in $C_s$, it is illustrated schematically in FIG. 13b that $V_c$ changes from the solid plot 231 to the dashed plot 232 and in FIG. 13c that $V_{osc}$ changes from the solid plot 233 to the dashed plot 234. The output from the AMV is transferred to a counter 239, and by counting the number of oscillations within a certain count time 235, the frequency of $V_{osc}$ may be determined. Monitoring the change in $V_{osc}$, a change in the capacitance of the sensor may therefore be determined and an occurrence of a leak may be reported. FIG. 13c illustrates a situation where the number of pulses counted within the count time 235 changes from N to N'. For small variations in sensor capacitance, the corresponding change in the measured frequency is, $$\Delta f \cong -A \frac{N'-N}{N} \frac{1}{RC_s},$$

and the corresponding relative change in capacitance is approximately given by $$\frac{\Delta C_s}{C_s} \cong A \frac{N'-N}{N}. \qquad \text{Eqn. (5)}$$

As an alternative to an astable multivibrator, other types of oscillators may be used, such as a Colpitts oscillator or a Hartley oscillator, which are also known by the person skilled in the art. For the Colpitts oscillator, which is the preferable of the two, the oscillation frequency is determined approximately as in FIG. 1 by an inductor ($L_c$) and the series connection of two capacitors $C_{adh1}$ and $C_{adh2}$.

The output of the counter 239 may be transferred to a micro-controller 240, which compares the count with a predetermined time-variation in the count corresponding to time-variation in the changes of $C_s$ and an occurrence of a leak. The counter may be reset to count at regular intervals. The reset may be carried out internally in the counter or as illustrated in FIG. 13a, the micro-controller 240 may send a reset signal 241 to reset the counter at regular intervals.

Alternatively, the counter may run asynchronously with the count being captured by the micro-controller at predefined intervals. The counter or parts of the counter may be integrated in the micro-controller.

The output of the micro-controller 240 is further transferred to a communication unit 242. The communication unit may report wirelessly the state of the sensor to an event-handling device, a gate-way or a service centre. Alternatively, the communication unit may report an occurrence of a leak to the user by e.g. an acoustic signal, a vibration signal or the like.

Examples of component values for a typical design are a sensor capacitance of $C_s=20$ pF, a resistor $R=5$ k$\Omega$, a constant $A=\frac{1}{2}$, a count rate $N=1000$ corresponding to a count time of $N \times RC_s/A=200$ µs, which can be achieved for a counter with a bit resolution $\geqq 10$ bit, and a change in the count of $N'-N=1$.

According to Eqn. (5), with these numbers, the resolution of capacitance change is $$\frac{\Delta C_s}{C_s} = 0.0005.$$

The resolution of measuring the capacitance can be increased e.g. by increasing the bit resolution of the counter. The count time and the frequency need to be adjusted accordingly. As an example, with a 16 bit resolution the count rate is $N=65536$ corresponding to a count time of 13 ms and a $$\frac{\Delta C_s}{C_s} \text{ of } 8 \times 10^{-8}.$$

The electrical coupling 243 and 243' between the capacitance of the sensor and the AMV may be capacitive or galvanic.

There are a number of other methods of measuring capacitance from the time constant of a resistor-capacitor ($RC_s$) circuit. Such methods include: an ac bridge method, charge and decharge methods, a switched capacitor technique and capacitance-to-phase angle conversion (see e.g. Ref. A. Ashrafi et al., Rev. Sci. Instrum., Vol. 70 (1999), p. 3483 and references therein).

In cases where $\Delta C_s \ll C_s$, compensation of the fixed offset capacitance can be made and higher measurement accuracy can be achieved. One measurement scheme employs a direct-to-digital capacitive sensor readout circuit based on a capacitance-controlled relaxation oscillator in which the fixed offset is cancelled within an analogue oscillator. The reference capacitance ($C_{ref}$) is subtracted from the sensor capacitance ($C_s$) multiplied by a constant (b) and measurements of a pulse duration proportional to $R' \times (C_s - bC_{ref})$ with R' being a resistor are carried out. The change in pulse duration changes the duty cycle of a square-wave oscillator, which is converted to a digital number by a counter (see Z. Ignjatovic and M. F. Bocko, IEEE Sensors Journal, Vol. 5 (2005), p. 403 and other measurement schemes reported in references therein).

FIGS. 15a-15d illustrate several embodiments of attachment of an ostomy bag 153; 158; 165 and 175 (pouch) onto a bandage 136; 137; 138 and 139 (adhesive wafer) comprising different embodiments of adhesive leak sensors. The pouches are welded to the topfoils 161; 166 and 176 of the bandages.

Figure 15:
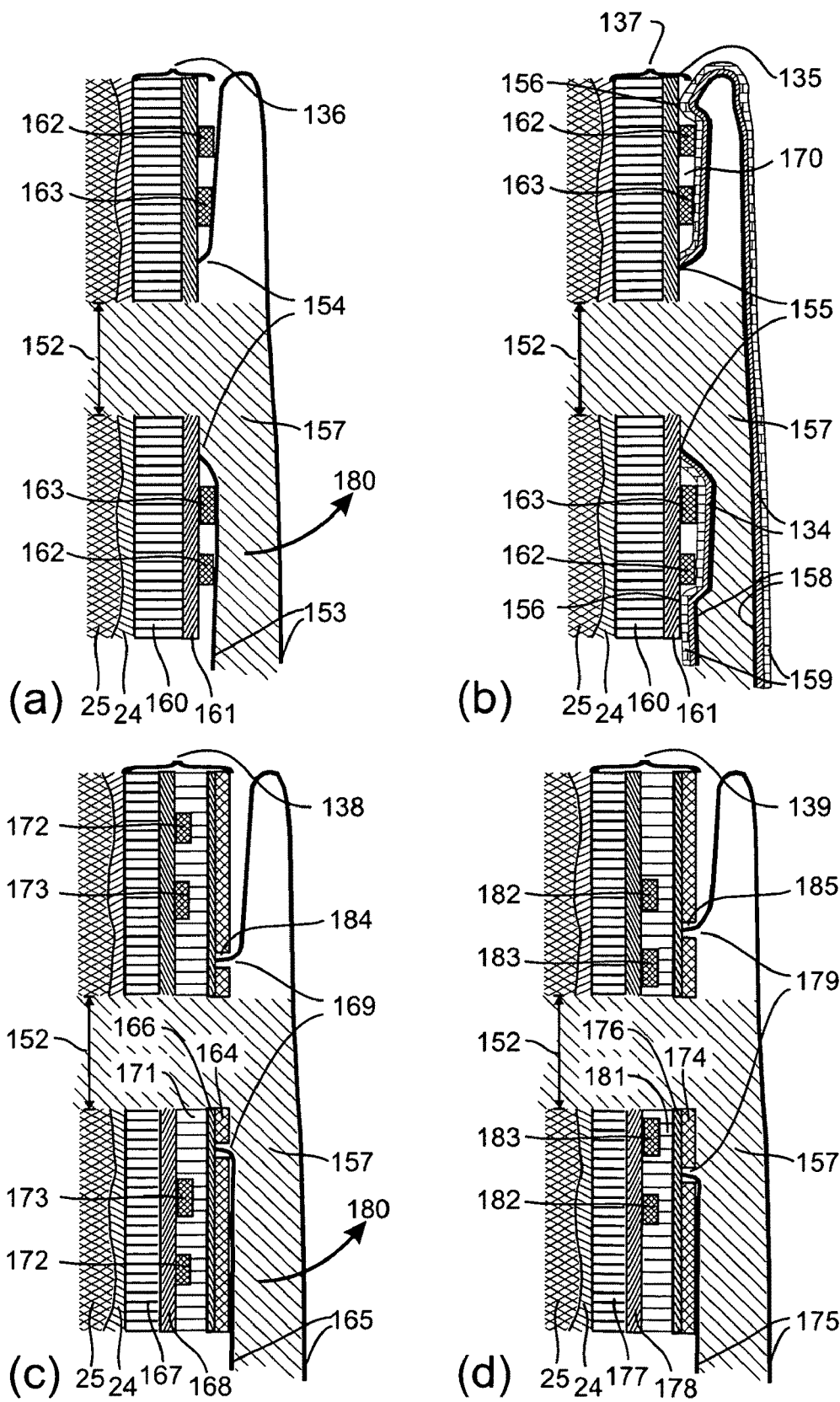
FIG. 15a, shows an embodiment of an ostomy appliance according to the invention.
FIGS. 15b, 15c and 15d show different embodiments of an ostomy appliance according to the invention illustrating means of reducing the influence of capacitive coupling from outside sources.

The embodiment illustrated in FIG. 15(a) comprises an adhesive 160 attached to the surface of the outer skin of a person 24, a topfoil 161, a first electrically conductive pattern comprising two ring-electrodes 162 and 163, a pouch 153 attached to the topfoil 161 by a weld seam 154. From the opening 152, a substance 157 may fill or partly fill the pouch.

The substance 157 is typically a stool from a stoma, which is electrically conductive, and causes a considerable increase in the capacitive coupling between the two ring-electrodes 162 and 163.

FIG. 15(b) illustrates an embodiment with a pouch attached to the topfoil of an adhesive. Isolation means 159 are provided around the pouch 158. The isolation means may comprise a material with a low dielectric value such as polyethylene, fluorinated benzoate copolymer or a substance embedding dry air such as a nanoporous dielectric material, a foam, a non-woven or the like. Additionally, the outer side of the pouch 158 or the part of the pouch covering the electrodes 162 and 163 may be coated by an electrically conductive film 134. Thus, a fixed capacitance is introduced comprising the first electrically conductive pattern, i.e. the inner and outer ring-electrodes 163 and 162, the dielectric material 159 and the electrically conductive coating of the outer side of the pouch 134. The coating may be evaporated, sputtered or sprayed aluminium, conducting polymers like polyaniline, polypyrrole, ethylenedioxythiophene, poly(p-pyridyl vinylene); or amorphous conducting carbon films, films of conducting carbon fibres or polymer-conducting-carbon-black. Alternatively, the foil of the pouch 158 may be laminated with a conductive layer 134. In addition the foil of the pouch 158 and the conductive layer 134 may be laminated with the isolation means 159.

The isolation means reduces the capacitive coupling through the electrically conductive substance 157. A first weld seam 155 attaches the pouch to the topfoil 161 of the bandage 137. The first weld seam is provided between the opening 152 and the inner ring electrode 163. A second weld seem 156 attaching another area of the pouch to the topfoil 161 is provided between the outer circumference 135 of the bandage and the outer ring electrode 162. Thus a pocket 170 is formed containing the inner and outer electrode ring. This advantageously prevents capacitive coupling, for example when the substance 157 is displaced over the electrically conductive pattern 162 and 163 or a region in the vicinity thereof.

FIG. 15(c) illustrates an alternative embodiment with an adhesive 167 attached to the surface of the outer skin 24 of a person, a first foil 168, a first electrically conductive pattern comprising an outer ring-electrode 172 and an inner ring-electrode 173, a second adhesive or other dielectric material 171, a topfoil 166, a shield layer 164 comprising a second electrically conductive pattern, a pouch 165 attached to the topfoil 166 of the bandage 138 by a weld seam 169. At the weld position, a groove 184 in the shield layer 164 may be made to enable the weld. The second electrically conductive pattern formed in the shield layer 164 prevents capacitive coupling between the electrically conductive substance 157 and the first electrically conductive pattern. Instead a fixed capacitance is introduced consisting of the first electrically conductive pattern, i.e. the inner and outer ring-electrodes 173 and 172, the dielectric material 171 and the shield layer 164 comprising the second electrically conductive pattern. For a first electrically conductive pattern of two ring-electrodes, the fixed capacitance is approximately given by eqn. (3).

The second electrically conductive pattern can be formed of many different types of materials, for example metals like silver, gold, aluminium or copper or paste of silver or aluminium; conducting polymers like polyaniline, polypyrrole, ethylenedioxythiophene, poly(p-pyridyl vinylene); or amorphous conducting carbon films, films of conducting carbon fibres or polymer-conducting-carbon-black. Materials may also be doped semiconductors such as tin oxide ($SnO_2$), zinc oxide ($ZnO_2$), indium tin oxide (ITO) or the like. The second electrically conductive pattern may be made by, but not limited to, methods such as screen-printing or tampon printing using silver paste or aluminium paste, or inkjet-produced patterns of solid copper or ink of highly conducting substances.

FIG. 15(d) illustrates an alternative embodiment, where the first electrically conductive pattern formed of outer ring-electrode 182 and inner ring-electrode 183, is positioned close to the opening 152.

The bandage is attached to the surface 24 of the outer layer of the skin by a first adhesive 177 which is disposed on a first foil 178 arranged opposite the skin, on the distal side of the first adhesive. The outer ring-electrode 182 and the inner ring-electrode 183 forming the first electrically conductive pattern are printed on top of the first foil. Between the first foil 178 and the top film 176 there is disposed a second adhesive 181 or other dielectric material. On the top film 176, opposite the second adhesive there is provided a shield layer 174 in the form of a second electrically conductive pattern.

The extent of the foils 161, 168, and 178 may be limited to an area covering the first electrically conductive pattern or they may be extended over the whole bandage or beyond the extent of the bandage. Similarly, the second electrically conductive patterns 164 and 174 may be extended over the whole bandage or they may be bounded by an area sufficiently overlapping the area of the first electrically conductive pattern to prevent capacitive coupling from an electrically conductive substance 157.

By providing a groove 185 in the shield layer 174 a weld seam 179 can be provided therein attaching the pouch 175 to the top film 176 of the bandage 139. The weld seam 179 is positioned between the two electrically conductive rings 182 and 183 when looking at the bandage in a top view. This reduces the effect of capacitive coupling at the weld seam.

The weld seams 154, 155, 156, 169 and 179 may be made by means of heat welding, ultrasonic welding, high frequency welding, transmission laser welding or other suitable welding techniques. Alternatively, the weld seams may be achieved by means of gluing.

Figure 16A:
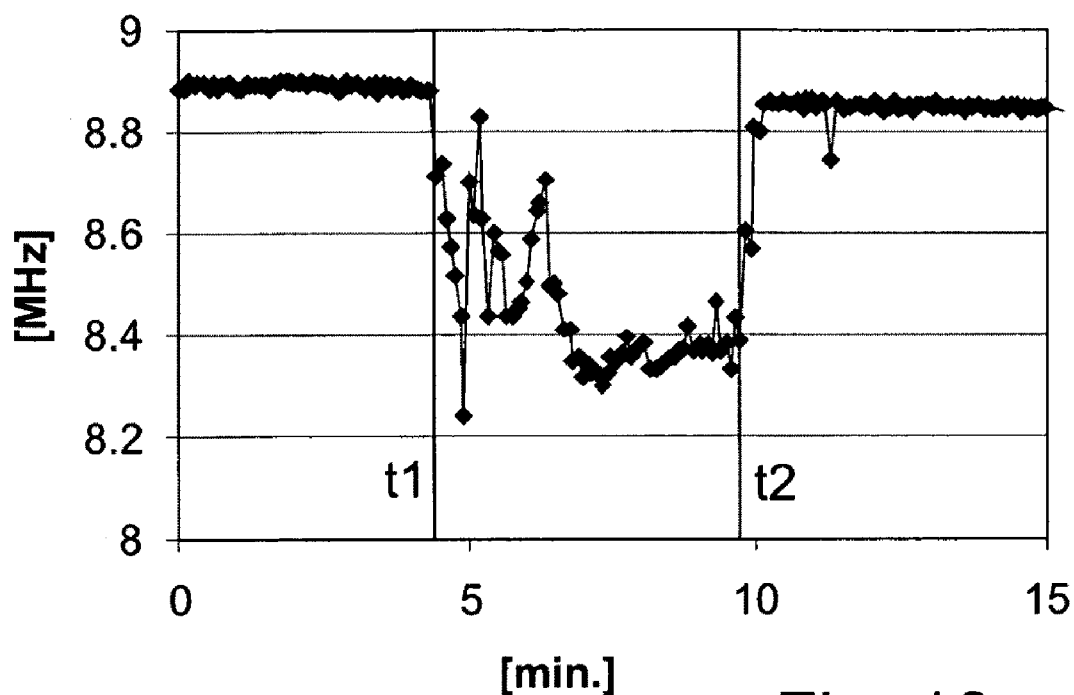
FIGS. 16a and 16b show effects of capacitive coupling between the environment above the top-foil and the electrical conductors as plots of the resonance frequency as function of time for an embodiment of the present invention where no shield layer is provided on a dressing according to the invention and where a shield layer has been provided on a dressing according to the invention, respectively.
Figure 16B:
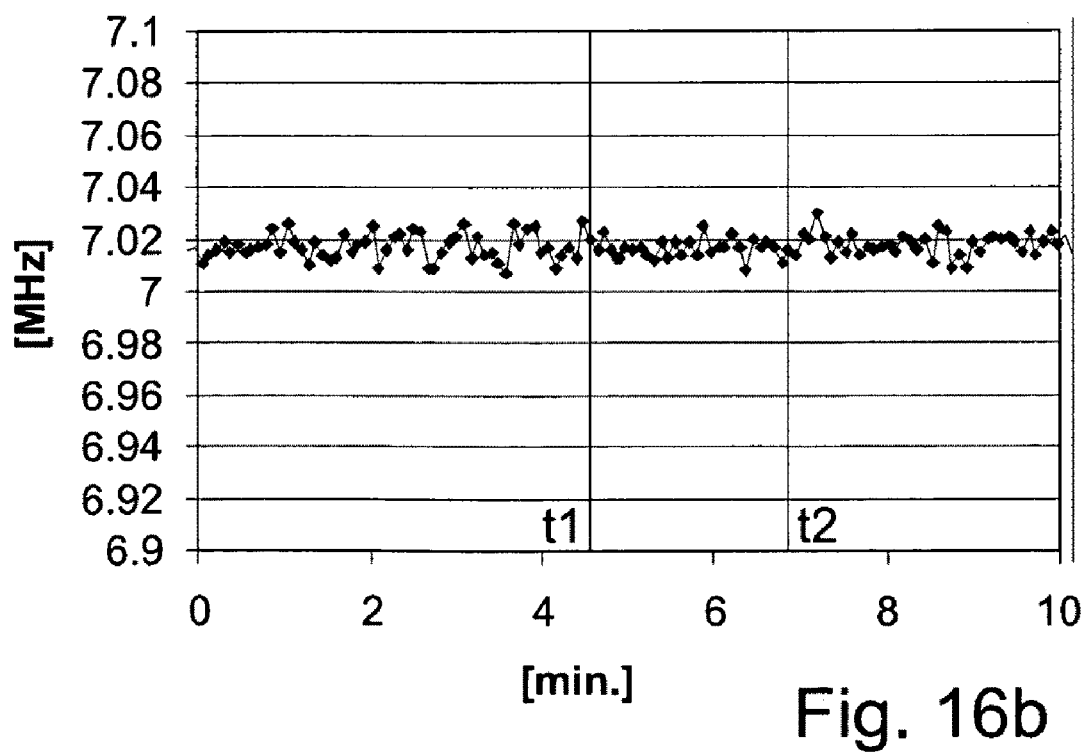

FIGS. 16a and 16b illustrate an example of the effect of the shield layers described with respect to FIGS. 15a-15d. FIGS. 16a and 16b plot the changes in the adhesive leak sensor signal (i.e. the resonance frequency [MHz]) as a result of lifting up in an ostomy bag welded to the adhesive and filled with a liquid (80 ml 0.9% NaCl aqueous solution) for a period of time [min].

FIG. 16a is a plot for a sensor configuration without shield layer as in FIG. 15a. Initially, the liquid causes capacitive coupling to the adhesive leak sensor. When the bag is lifted up at t1, the capacitive coupling is removed, and when the bag is lifted down again at t2, the capacitive coupling is re-established. This shows a significant change in the resonance frequency between t1 and t2.

FIG. 16b is a similar plot for a sensor configuration with shield layer, as shown in FIG. 15c, where the bag is lifted up at t1 and lifted back down again at t2.

For an ostomy product with a configuration as illustrated schematically in FIG. 15a, when the bag is lifted down, the liquid causes capacitive coupling between the two electrically conductive rings 162 and 163. Lifting the bag up in the direction as indicated by the arrow 180, removes this capacitive coupling.

For the configuration as illustrated in FIG. 15a without shield layer, this creates large changes in the sensor signal (~0.5 MHz) as observed in FIG. 16a between t1 and t2. Depending on the sensor assembly and set-up, these changes may be similar to or even larger than a leak for this configuration. For a configuration with a shield layer as shown in FIG. 15c, there is no or negligible effect of lifting the bag up and down in the direction as indicated by arrow 180 in FIG. 15c and as observed in FIG. 16b between t1 and t2.

Figure 17:
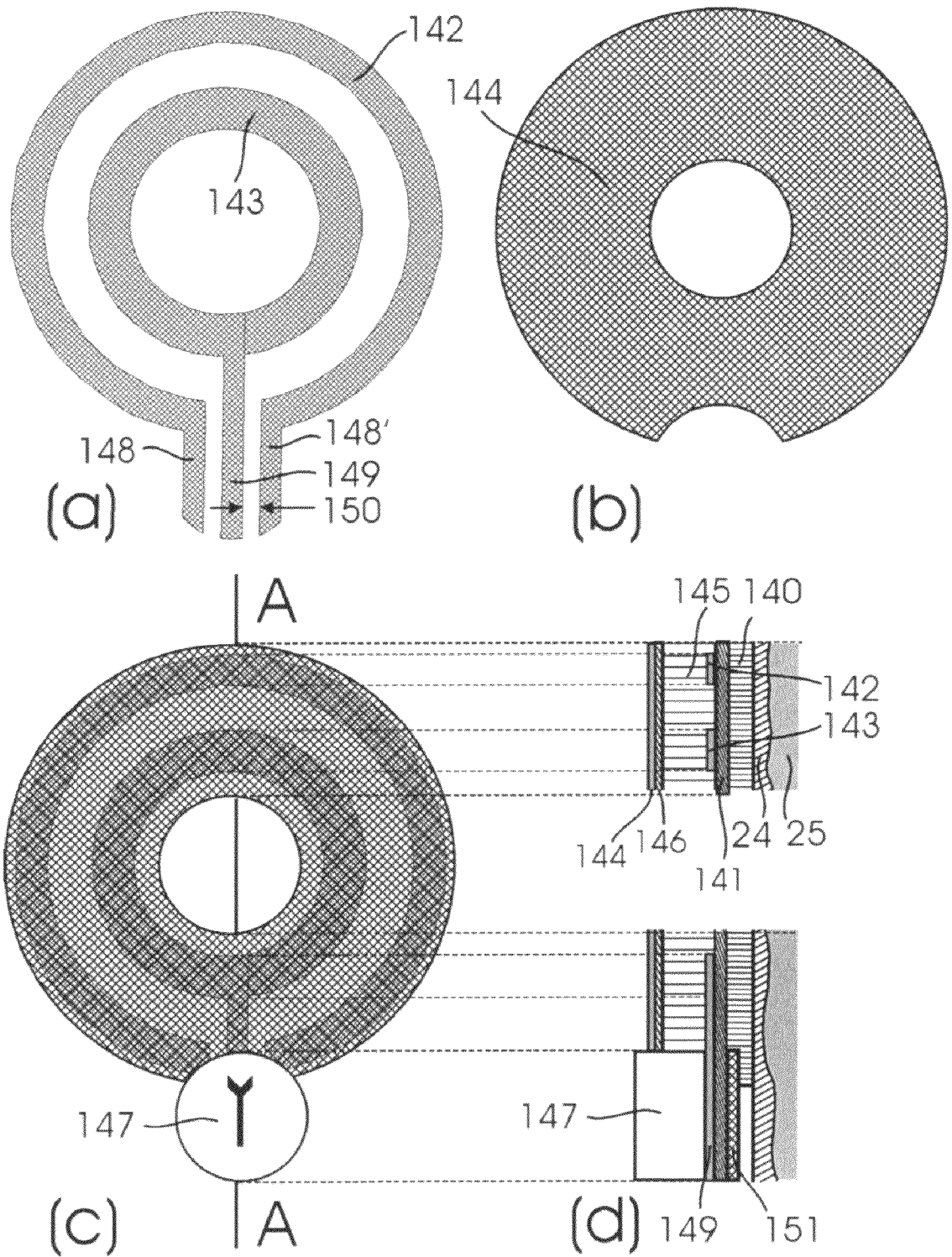
FIGS. 17a, 17b, 17c and 17d show an alternative embodiment of a bandage of the present invention with a top view of the conductive patterns for the two ring capacitors, the electrical shield layer, the alignment of the conductive patterns for the two ring electrodes, and in cross section the embodiment along the line A-A.

FIGS. 17a-17d shows an alternative embodiment of a bandage of the present invention. FIG. 17a shows in top view the conductive patterns for the two ring capacitors 142 and 143. FIG. 17b shows in top view the electrical shield layer 144. FIG. 17c illustrates the alignment of the conductive patterns for the two ring electrodes 142 and 143, the shield layer 144 and a reader 147. FIG. 17d shows in cross section the embodiment along line A-A in FIG. 17c.

Electrical connection to the outer ring electrode 142 is made by the two conductive fingers 148 and 148' and electrical connection to the inner ring electrode 143 is made by the conductive finger 149. The reader 147 is electrically connected to the two ring capacitors 142 and 143 via the conductive fingers 148, 148' and 149. The connection may be galvanic or capacitive. Alternatively, the fingers may comprise a coil-like pattern and the electrical connection may be inductive.

The foil 141 comprising the electrically conductive pattern whereon the outer and inner ring electrodes 142, 143 are printed extends beyond the periphery of the shield layer. It is embedded between a first adhesive layer 140 and a second dielectric layer 145, which may be a second adhesive. An additional layer 151 may support the foil mechanically. The additional layer 151 may be an extension of the first adhesive 140 and it may or maybe not be attached to the surface of the skin 24. The topfoil 146 comprises the shield layer 144.

The distance 150 between the two fingers 148' and 149, and the equivalent distance between 148 and 149, should be large enough to exhibit small parasitic capacitance and inductance, but small enough to enable safe detection of a potential leak at this position. The distance is preferably between 1/20 and 5 times the distance between the outer radius of the inner ring electrode and the inner radius of the outer ring electrode, more preferably between 1/8 and 2 times this distance and even more preferably between 1/4 and 1 times this distance.

The invention claimed is:

1. A method for detecting detachment of a dressing, which is applied to a surface of an at least partly electrically conductive object, said dressing comprising an adhesive for attaching the dressing to the electrically conductive object and at least two electrodes arranged in a distance from the electrically conductive object, and wherein,
   a voltage is applied to the first and second electrode establishing an electrical circuit comprising a first capacitor between the first electrode and the electrically conductive object and a second capacitor between the second electrode and the electrically conductive object,
   changes of the capacitance between at least one of the first and the second electrode and the electrically conductive object are detected by measuring the change in the time constant of the electrical circuit, and
   an alarm is activated when the changes of the capacitance reach a predetermined value.

2. A method according to claim 1, wherein the changes of the capacitance are detected by monitoring the frequency response of the electrical circuit.

3. A method according to claim 2, wherein monitoring the frequency response of the electrical circuit is made by performing a frequency sweep at regular intervals while measuring the response from the electrical circuit.

4. A method according to claim 2, wherein monitoring the frequency response of the electrical circuit is made by applying an electrical impulse to the electrical circuit and subsequently measuring the response from the electrical circuit.

5. A method according to claim 1, wherein the time constant of the electrical circuit is detected by connecting an astable multivibrator to the first and second capacitor and at least one resistor, and repetitively counting the change in the number of output pulses from the astable multivibrator within a predetermined time interval.

6. A method according to claim 1, wherein the time constant of the electrical circuit is detected by connecting a Colpitts oscillator to the first and second capacitor and at least one inductor, and repetitively counting the change in the number of output pulses from the Colpitts oscillator within a predetermined time interval.

7. A dressing suitable for applying the method of claim 1, comprising an adhesive body having a proximal adhesive surface, at least a first and a second electrode arranged on the dressing so that at least a part of the adhesive body is arranged between the proximal adhesive surface and the first and second electrodes, wherein a first width of the first electrode and a second width of the second electrode are larger than the respective first thickness and second thickness of the respective first and second electrode in at least one area.

8. A dressing according to claim 7, wherein the first and the second width are uniform along the extent of the first and the second electrode, respectively.

9. A dressing according to claim 7, wherein the second electrode at least partly encircles the first electrode.

10. A dressing according to claim 7, wherein the first and the second electrode are formed as a first and a second circular track, respectively and where the inner diameter of the second circular track is larger than the outer diameter of the first circular track.

11. A dressing according to claim 7, wherein an inductance is connected to at least one of the first and the second electrode.

12. A dressing according to claim 7, wherein the first and second electrode are electrically isolated from the adhesive body.

13. A dressing according to claim 7, wherein the at least first and second electrode are arranged at least partly embedded in the adhesive body.

14. A dressing according to claim 7, wherein the at least first and second electrode are arranged on the distal side of the adhesive body.

15. A dressing according to claim 7, wherein the first electrode and the second electrode are printed on a flexible film.

16. A dressing according to claim 7, wherein an encircling groove is formed in the proximal adhesive surface of the adhesive body.

17. A dressing according to claim 16, wherein the encircling groove is arranged opposite one of the electrodes.

18. A dressing according to claim 16, wherein a first electrically conductive ring and a second electrically conductive ring are arranged in the encircling groove, and wherein the first electrically conductive ring is electrically connected to the first electrode and the second electrically conductive ring is electrically connected to the second electrode.

19. A dressing according to claim 7, wherein a multitude of electrodes encircle the first and the second electrode.

20. A dressing according to claim 7, wherein the dressing is a base plate for an ostomy bag.

21. A dressing according to claim 7, wherein a first upper electrode and a second upper electrode electrically connected by a second inductance are arranged on the distal side of the first and second electrode.

22. A dressing according to claim 7 further comprising a dielectric layer on the distal side of the aforesaid electrodes and an electrical shield layer on top of the dielectric layer.

\* \* \* \* \*

UNITED STATES PATENT AND TRADEMARK OFFICE
CERTIFICATE OF CORRECTION

PATENT NO. : 8,398,603 B2  
APPLICATION NO. : 12/224507  
DATED : March 19, 2013  
INVENTOR(S) : Carsten Thirstrup et al.

Page 1 of 1

It is certified that error appears in the above-identified patent and that said Letters Patent is hereby corrected as shown below:

On the Title Page, the PCT priority date is incorrect.  
Please correct page 1, to present:

Item "(22) PCT Filed: February 28, 2007"

Signed and Sealed this  
Seventh Day of May, 2013

Teresa Stanek Rea  
*Acting Director of the United States Patent and Trademark Office*